(12) United States Patent
Hata et al.

(10) Patent No.: US 11,567,080 B2
(45) Date of Patent: Jan. 31, 2023

(54) DIAGNOSTIC AGENT AND MEDICINE COMPRISING ADAMTS13 AS MAIN INGREDIENT

(71) Applicants: Kyoto University, Kyoto (JP); KM BIOLOGICS CO., LTD., Kumamoto (JP)

(72) Inventors: Koichiro Hata, Kyoto (JP); Shinji Uemoto, Kyoto (JP); Hirofumi Hirao, Kyoto (JP); Toyonari Kubota, Kyoto (JP)

(73) Assignees: KYOTO UNIVERSITY, Kyoto (JP); KM BIOLOGICS CO., LTD., Kumamoto (JP)

( * ) Notice: Subject to any disclaimer, the term of this patent is extended or adjusted under 35 U.S.C. 154(b) by 661 days.

(21) Appl. No.: 16/066,111

(22) PCT Filed: Jan. 6, 2017

(86) PCT No.: PCT/JP2017/000316
§ 371 (c)(1),
(2) Date: Jun. 26, 2018

(87) PCT Pub. No.: WO2017/119498
PCT Pub. Date: Jul. 13, 2017

(65) Prior Publication Data
US 2020/0284793 A1    Sep. 10, 2020

(30) Foreign Application Priority Data

Jan. 8, 2016 (JP) .............. JP2016-002685

(51) Int. Cl.
*G01N 33/573* (2006.01)
*A61K 38/48* (2006.01)
*G01N 33/576* (2006.01)

(52) U.S. Cl.
CPC ....... *G01N 33/573* (2013.01); *A61K 38/4886* (2013.01); *G01N 33/576* (2013.01);
(Continued)

(58) Field of Classification Search
CPC ............... G01N 33/573; G01N 33/576; G01N 2333/96494; G01N 2800/08;
(Continued)

(56) References Cited

U.S. PATENT DOCUMENTS 10,202,633 B2   2/2019  Visentin et al.
2006/0251655 A1  11/2006  Soejima et al.
(Continued)

FOREIGN PATENT DOCUMENTS

CN    1701117      11/2005
CN    102533937    7/2012
(Continued)

OTHER PUBLICATIONS

CN 103808944. May 2014. English abstract. (Year: 2014).*
(Continued)

*Primary Examiner* — Renee Claytor
*Assistant Examiner* — Susan E. Fernandez
(74) *Attorney, Agent, or Firm* — Wenderoth, Lind & Ponack, L.L.P.

(57) ABSTRACT

New use of ADAMTS13 in the clinical filed is provided. The use of ADAMTS13 as a biomarker for monitoring the onset of liver damage, hepatic ischemia/reperfusion injury or the liver function after liver transplantation: a method of testing liver damage, a method of testing hepatic ischemia/reperfusion injury, or a method of testing the liver function after liver transplantation, each of the methods comprising measuring or monitoring the ADAMTS13 activity in a sample from a mammal; an agent for treating diseases selected from
(Continued)

the group consisting of liver damage, hepatic ischemia/ reperfusion injury and hepatic dysfunction after liver transplantation, which comprises ADAMTS13 or a mutant of ADAMTS13 as an effective ingredient.

12 Claims, 21 Drawing Sheets

(52) U.S. Cl.
CPC .............. *G01N 2333/96494* (2013.01); *G01N 2800/08* (2013.01); *G01N 2800/085* (2013.01)

(58) Field of Classification Search
CPC ....... G01N 2800/085; G01N 2800/245; A61K 38/4886; A61K 38/46; A61P 1/16; C12M 1/34; C12Q 1/37; C12N 9/64
See application file for complete search history.

(56) References Cited

U.S. PATENT DOCUMENTS

| | | | |
|---|---|---|---|
| 2006/0276388 A1* | 12/2006 | Christa | ............... A61P 3/06 514/1.8 |
| 2007/0015703 A1 | 1/2007 | Wagner et al. | |
| 2007/0275414 A1 | 11/2007 | Ono et al. | |
| 2008/0096221 A1 | 4/2008 | Ono | |
| 2009/0004673 A1 | 1/2009 | Ono et al. | |
| 2011/0229455 A1 | 9/2011 | Matthiessen et al. | |

FOREIGN PATENT DOCUMENTS

| | | | |
|---|---|---|---|
| CN | 103808944 A | * | 5/2014 |
| JP | 2009-539757 | | 11/2009 |
| JP | 2010-280571 | | 12/2010 |
| JP | 2012-103211 | | 5/2012 |
| JP | 2013-505270 | | 2/2013 |
| WO | 2005/062054 | | 7/2005 |
| WO | 2006/049300 | | 5/2006 |
| WO | 2007/088849 | | 8/2007 |
| WO | 2013/071168 | | 5/2013 |

OTHER PUBLICATIONS

Olivas, TP et al. Timing of microcirculatory injury from ischemia reperfusion. Plast. Reconstr. Surg. 2001. 107(3): 785-788. (Year: 2001).*
Malik, R et al. The role of non-parenchymal cells in liver growth. Seminars in Cell & Developmental Biology. 2002. 13: 425-431. (Year: 2002).*
Nishigori, N et al. von Willebrand factor-rich platelet thrombi in the liver cause sinusoidal obstruction syndrome following oxaliplatin-based chemotherapy. PLoS One. 2015. 10(11): e0143136. 17 pages. Published online Nov. 18, 2015. (Year: 2015).*
Ikeda, H et al. Prediction of hepatocellular carcinoma development by plasma ADAMTS13 in chronic hepatitis B and C. Cancer Epidemiol. Biomarkers Prev. 2011. 20(10): 2204-2211. (Year: 2011).*
George, JN. Measuring ADAMTS13 activity in patients with suspected thrombotic thromocytogenic purpura: when, how, and why? Transfusion. 2015. 55: 11-13 (Year: 2015).*
Partial Supplementary European Search Report dated Jul. 16, 2019 in corresponding European Patent Application No. 17736035.1.
Uemura et al., "Pivotal role of ADAMTS13 function in liver diseases", International Journal of Hematology, vol. 91, No. 1, 2010, p. 20-29.
Uemura et al., "Determination of ADAMTS13 and Its Clinical Significance for ADAMTS13 Supplementation Therapy to Improve the Survival of Patients with Decompensated Liver Cirrhosis", International Journal of Hepatology, vol. 2011, 2011, p. 1-12.
Cao et al., "Inflammatory cytokines inhibit ADAMTS13 synthesis in hepatic stellate cells and endothelial cells", Journal of Thrombosis and Haemostasis, vol. 6, No. 7, 2008, p. 1233-1235.

Ikeda et al., "Prediction of Hepatocellular Carcinoma Development by Plasma ADAMTS13 in Chronic Hepatitis B and C", Cancer Epidemiology, vol. 20, No. 10, 2011, p. 2204-2211.
Extended European Search Report dated Jan. 10, 2020 in corresponding European Patent Application No. 17736035.1.
Ko et al., "Relevance of ADAMTS13 to liver transplantation and surgery", World Journal of Hepatology, 2015, vol. 7, No. 13, pp. 1772-1781.
Soejima et al., "ADAMTS-13 cysteine-rich/spacer domains are functionally essential for von Willebrand factor cleavage", Blood, American Society of Hematology, 2003, vol. 102, No. 9, pp. 3232-3237.
Sadler, Evan J., "Von Willebrand factor, ADAMTS13, and thrombotic thrombocytopenic purpura", Blood, 112 (1): 11-18 (2008).
Clark, W.F., "Plasma Exchange for Renal Disease: Evidence and Use 2011", Journal of Clinical Apheresis, vol. 27, pp. 112-116 (2012).
Scully et al., "Guidelines on the diagnosis and management of thrombotic thrombocytopenic purpura and other thrombotic microangiopathies", British Journal of Haematology, vol. 158, pp. 323-335 (2012).
McCord, Joe M., "Oxygen-derived free radicals in postischemic tissue injury", The New England Journal of Medicine, 312 (3): 159-163 (1985).
Uemura et al., "Comprehensive analysis of ADAMTS13 in patients with liver cirrhosis", Thromb Haemost, vol. 99, pp. 1019-1029 (2008).
Fujimura, Yoshihiro, "ADAMTS13", The Journal of Japanese College of Angiology, 51 (3): 321-331 (2011), w/English abstract.
Matsumoto et al., "Liver Transplantation rescues a deficient state of von willebrand factor-cleaving protease activity in patients with liver cirrhosis due to congenital biliary atresia", Blood Transfusion Medicine, vol. 96, p. 636a (2000).
Uemura et al., "Localization of ADAMTS13 to the stellate cells of human liver", Blood, 106 (3): 922-924 (2005).
Chauhan et al., "ADAMTS13: a new link between thrombosis and inflammation", The Journal of Experimental Medicine, 205 (9): 2065-2074 (2008).
Zhao et al., "vonWillebrand factor—cleaving proteaseADAMTS13 reduces ischemic brain injury in experimental stroke", Blood, 114 (15): 3329-3334 (2009).
Fujioka et al., "ADAMTS13 gene deletion aggravates ischemic brain damage: a possible neuroprotective role of ADAMTS13 by ameliorating postischemic hypoperfusion", Blood, 115 (8): 1650-1653 (2010).
Moake, Joel L., "Von Willebrand Factor, ADAMTS13, and Thrombotic Thrombocytopenic Purpura", Seminars in Hematology, 41 (1): 4-14 (2004).
Larkin et al., "Severe Plamodium falciparum Malaria Is Associated with Circulating Ultra-Large von Willebrand Multimers and ADAMTS13 Inhibition", PLoS Pathogens, 5(3): 1-8 (2009).
Igaku, Saishin, "Control of arterial thrombosis: basic and clinical research on the VFW-GPIb axis-dependent thrombotic disorders, modulated by ADAMTS13", 64(2): 290-321 (2009), with English abstract.
Kandutsch et al., "Patterns of hepatotoxicity after chemotherapy for colorectal cancer liver metastases", European Journal of Cancer Surgery, 34(11): 1231-1236 (2008).
Khan et al., "Patterns of chemotherapy-induced hepatic injury and their implications for patients undergoing liver resection for colorectal liver metastases", Journal of Hepatobiliary Pancreatic Surgery, 16(2): 137-144 (2008).
Rubbia-Brandt et al., "Severe hepatic sinusoidal obstruction associated with oxaliplatin-based chemotherapy in patients with metastic colorectal cancer", Annals of Oncology, 15 (3): 460-466 (2004).
Hugenholtz et al., "An Unbalance Between von Willebrand Factor and ADAMTS13 in Acute Liver Failure: Implications for Hemostasis and Clinical Outcome", Hepatology, 58 (2): 752-761 (2013).
Ko et al., "Plasma ADAMTS13 Activity May Predict Early Adverse Events in Living Donor Liver Transplantation: Observations in 3 Cases", Liver Transplantation, 12 (5): 859-869 (2006).

(56) References Cited

OTHER PUBLICATIONS

Kume et al., "Hepatic stellate cell damage may lead to decreased plasma ADAMTS13 activity in rats", Federation of European Biochemical Societies, vol. 581, pp. 1631-1634 (2007).
Uemura et al., "Decreased Activity of Plasma ADAMTS13 May Contribute to the Development of Liver Disturbance and Multiorgan Failure in Patients with Alcoholic Hepatitis", Alcohol Clinical Experimental Research, 29(12): 264S-271S (2005).
International Search Report dated Feb. 7, 2017 in International (PCT) Application No. PCT/JP2017/000316.
International Preliminary Report on Patentability dated Jul. 5, 2018 in International (PCT) Application No. PCT/JP2017/000316.
Office Action dated Oct. 14, 2020 in corresponding Chinese Patent Application No. 201780005400.3 with English-language translation.
Translation of Office Action dated Mar. 31, 2020 in corresponding Chinese Patent Application No. 201780005400.3.
Extended European Search Report dated Jan. 27, 2022 in corresponding European Patent Application No. 21211497.9, 9 pages.

* cited by examiner

[Fig. 10]
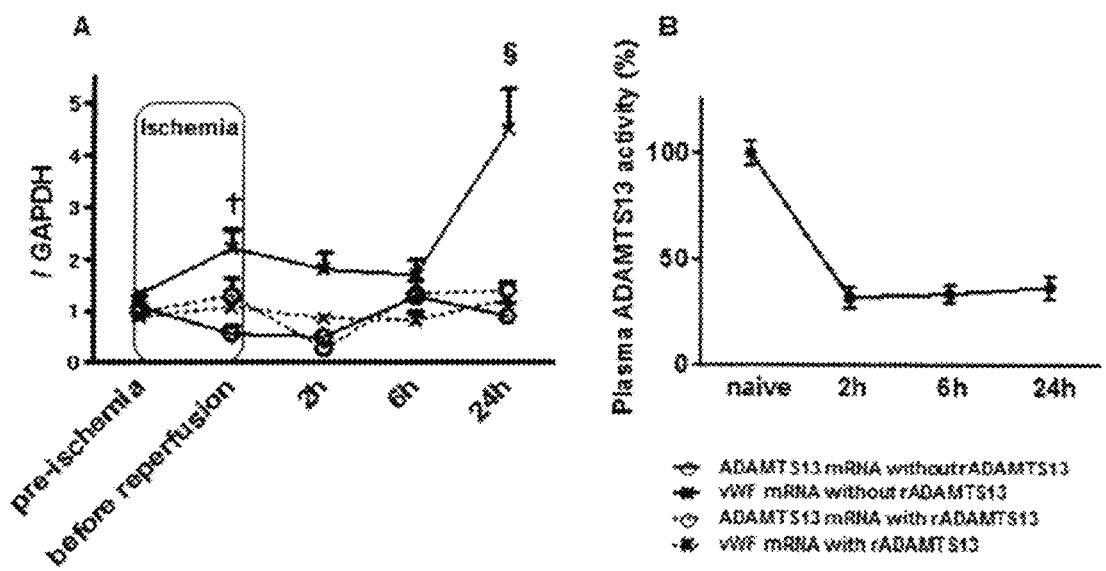
[Fig. 11]
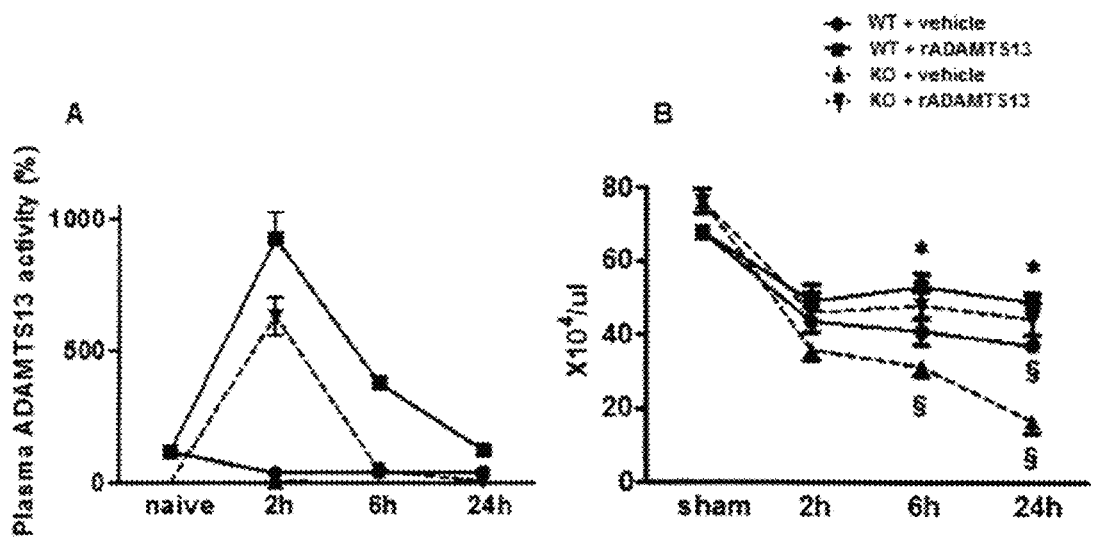

[Fig. 12]
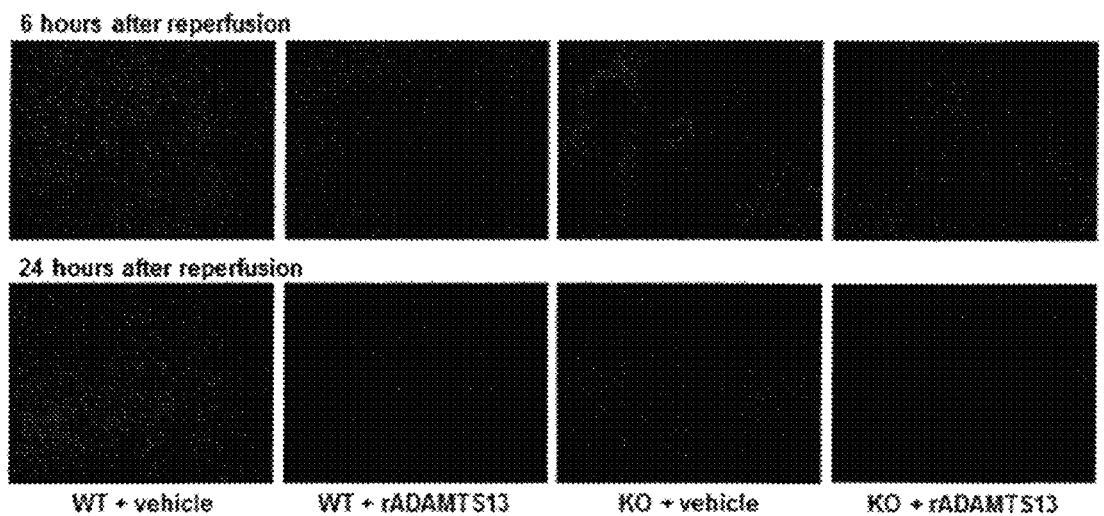
[Fig. 13]
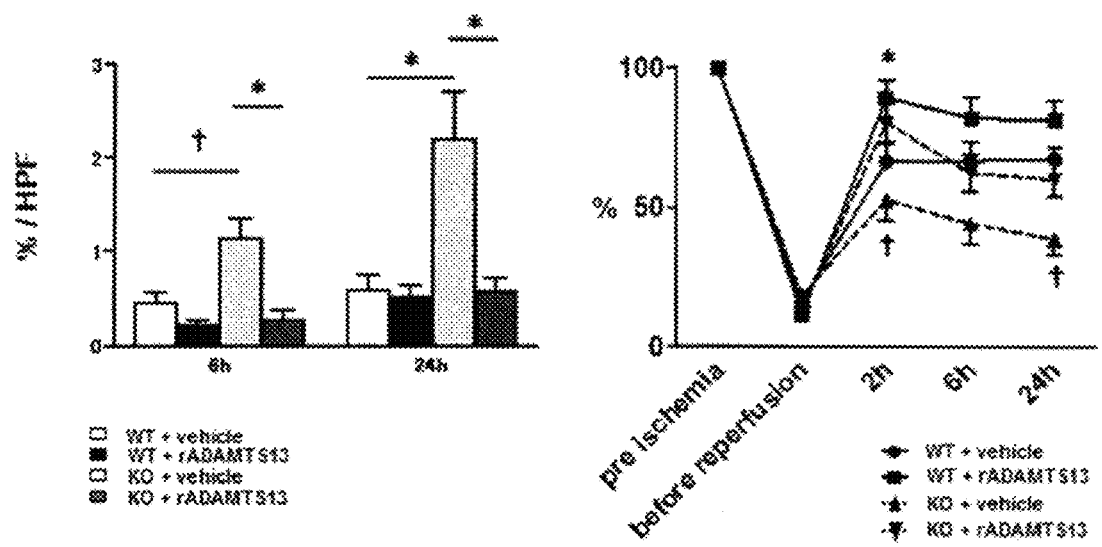

[Fig. 14]
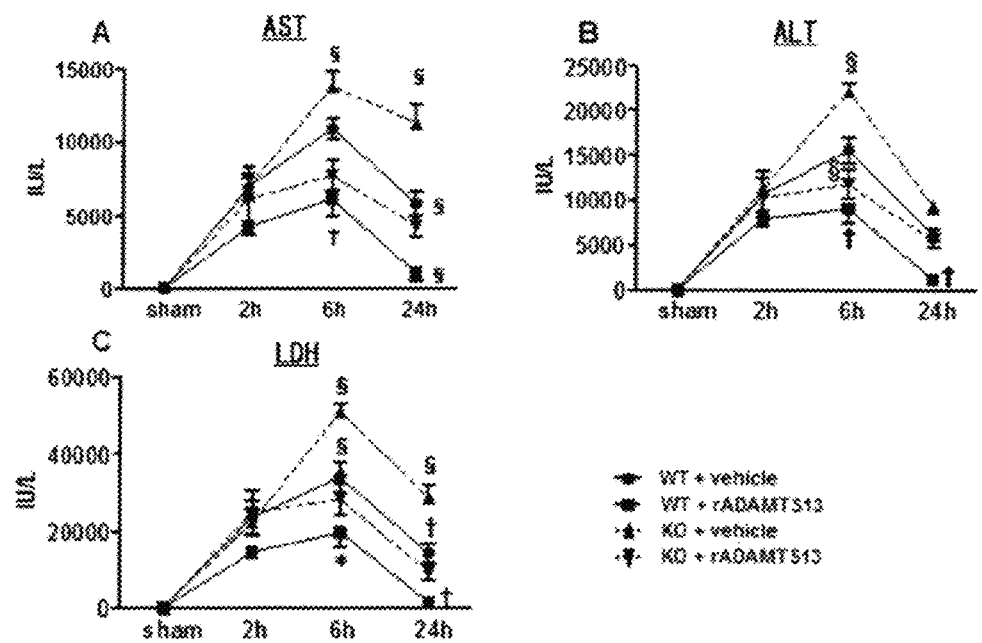
[Fig. 15]
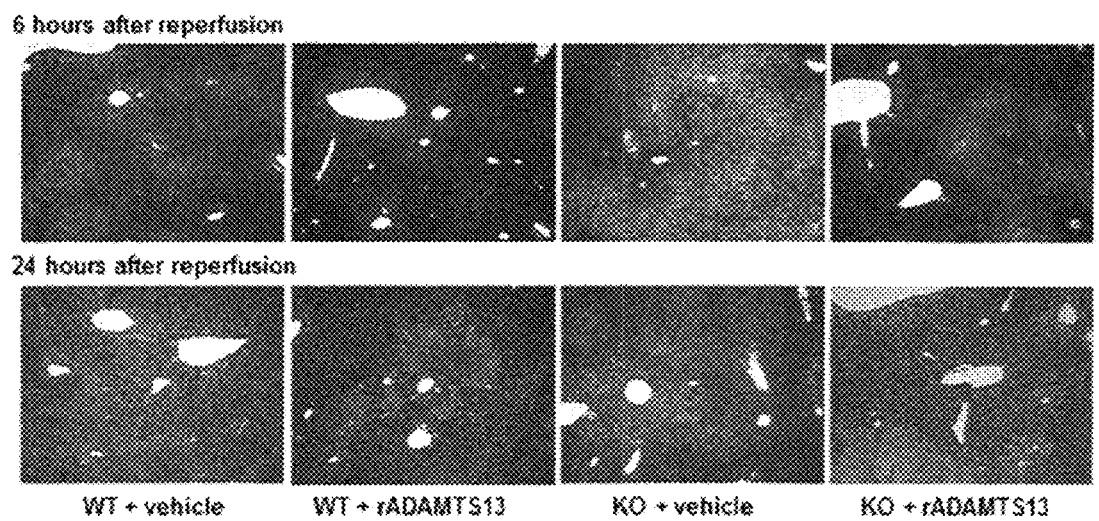

[Fig. 16]
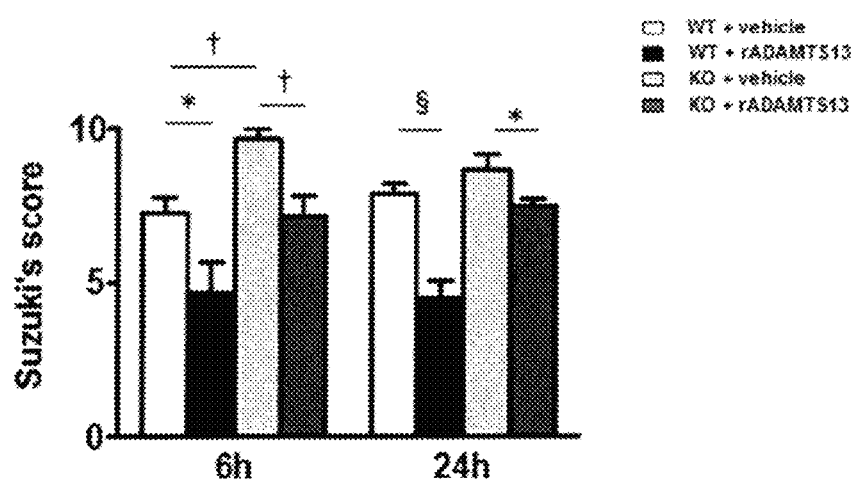

[Fig. 17]
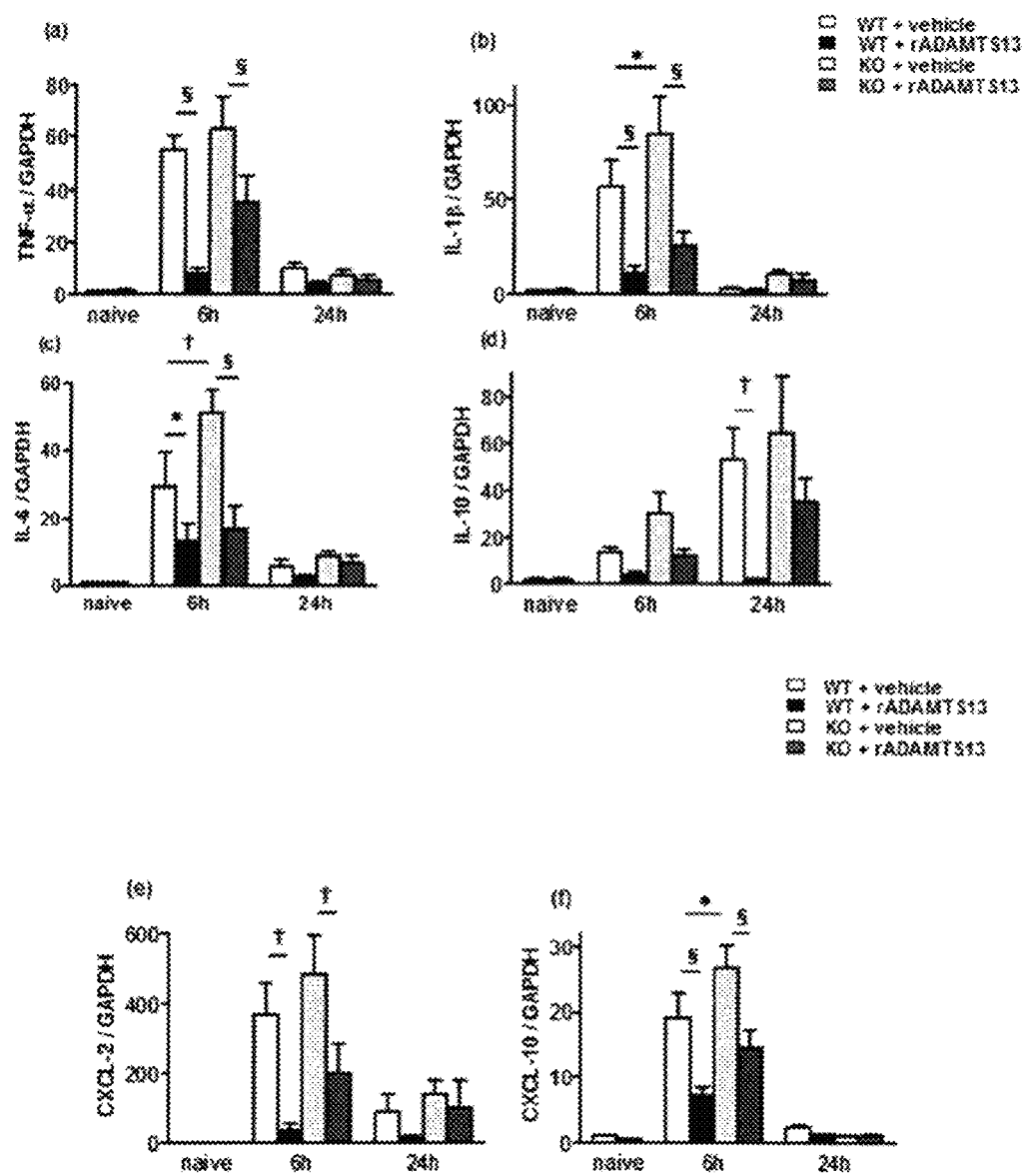

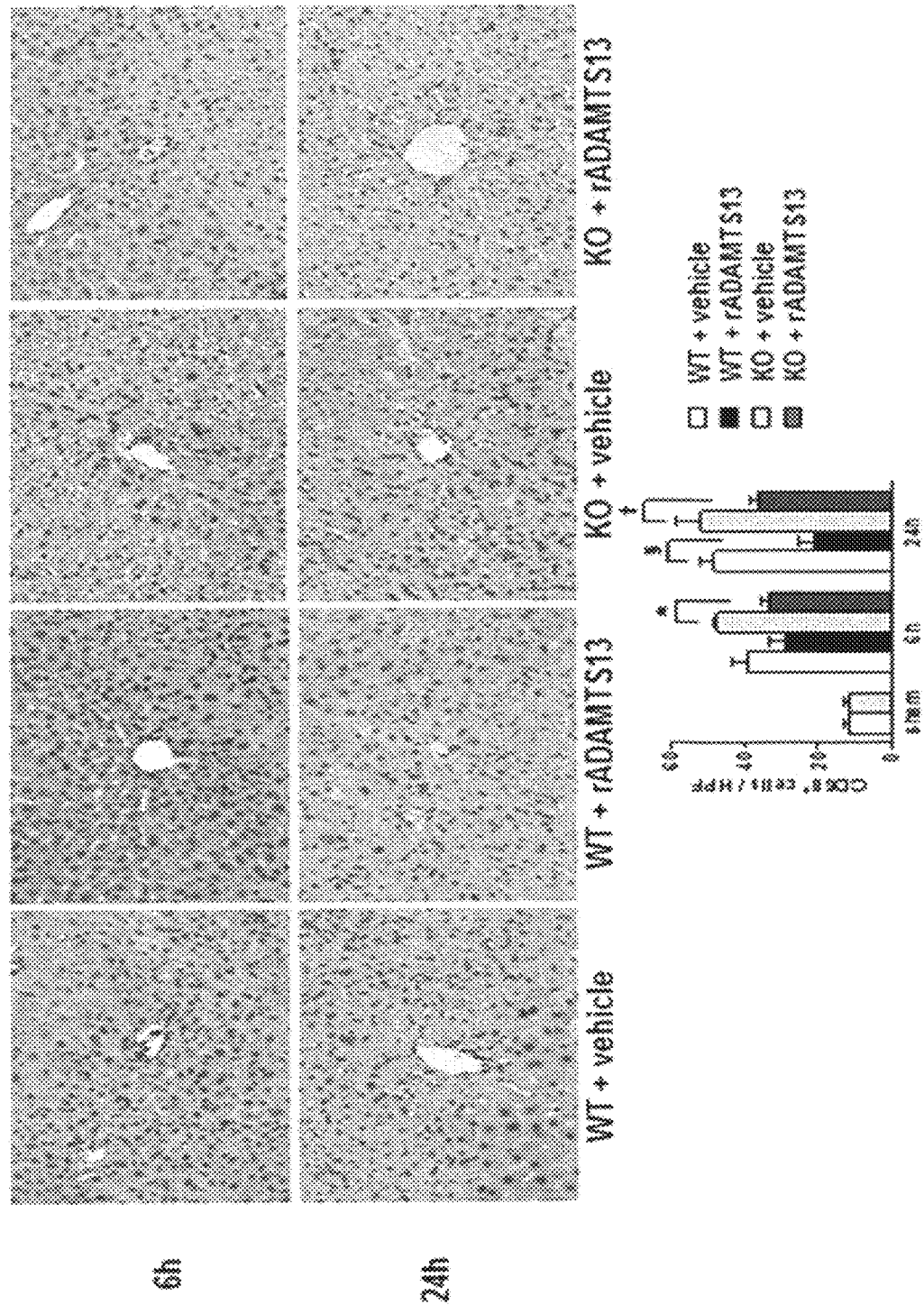
[Fig. 18]

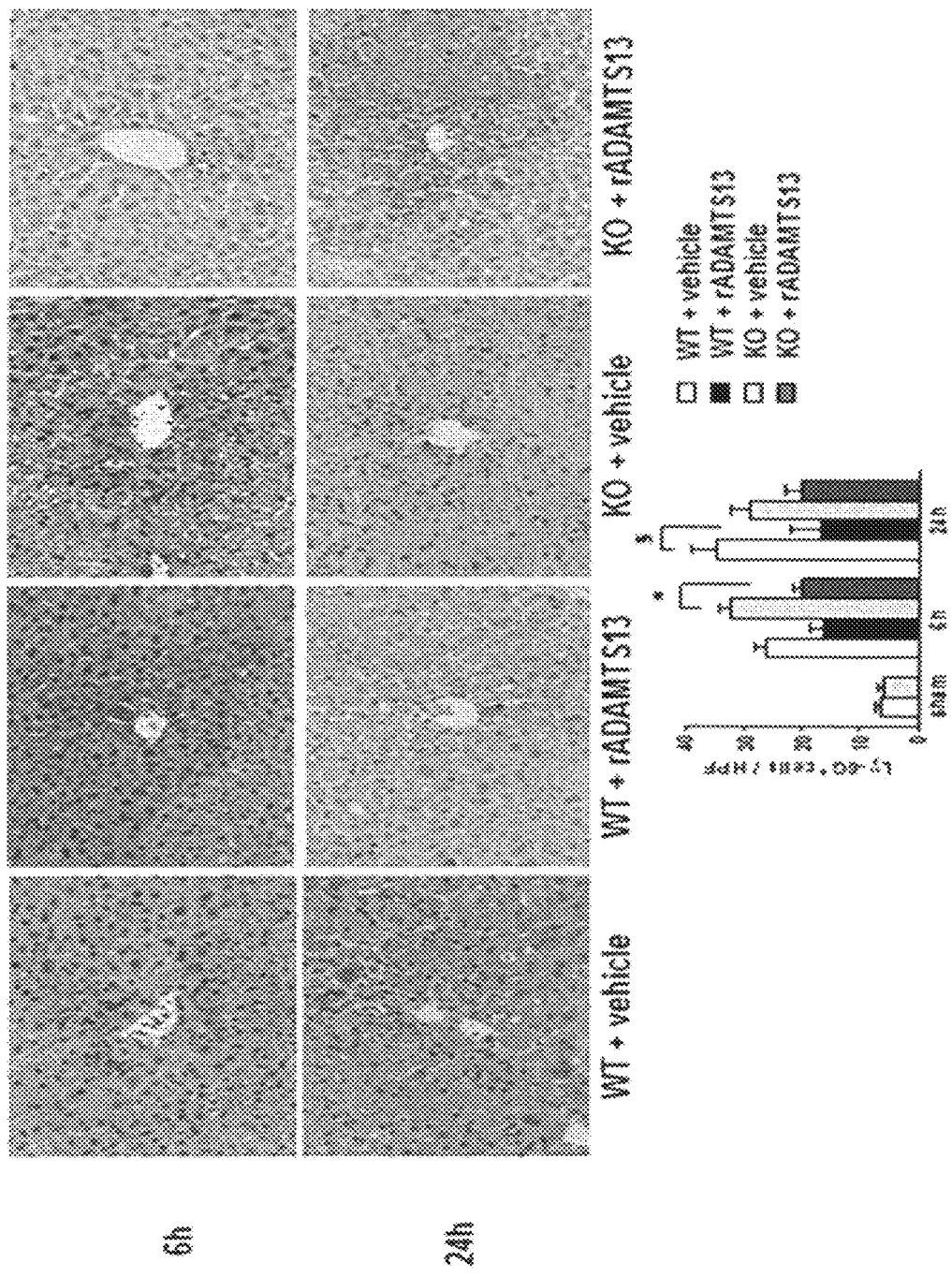
[Fig. 19]

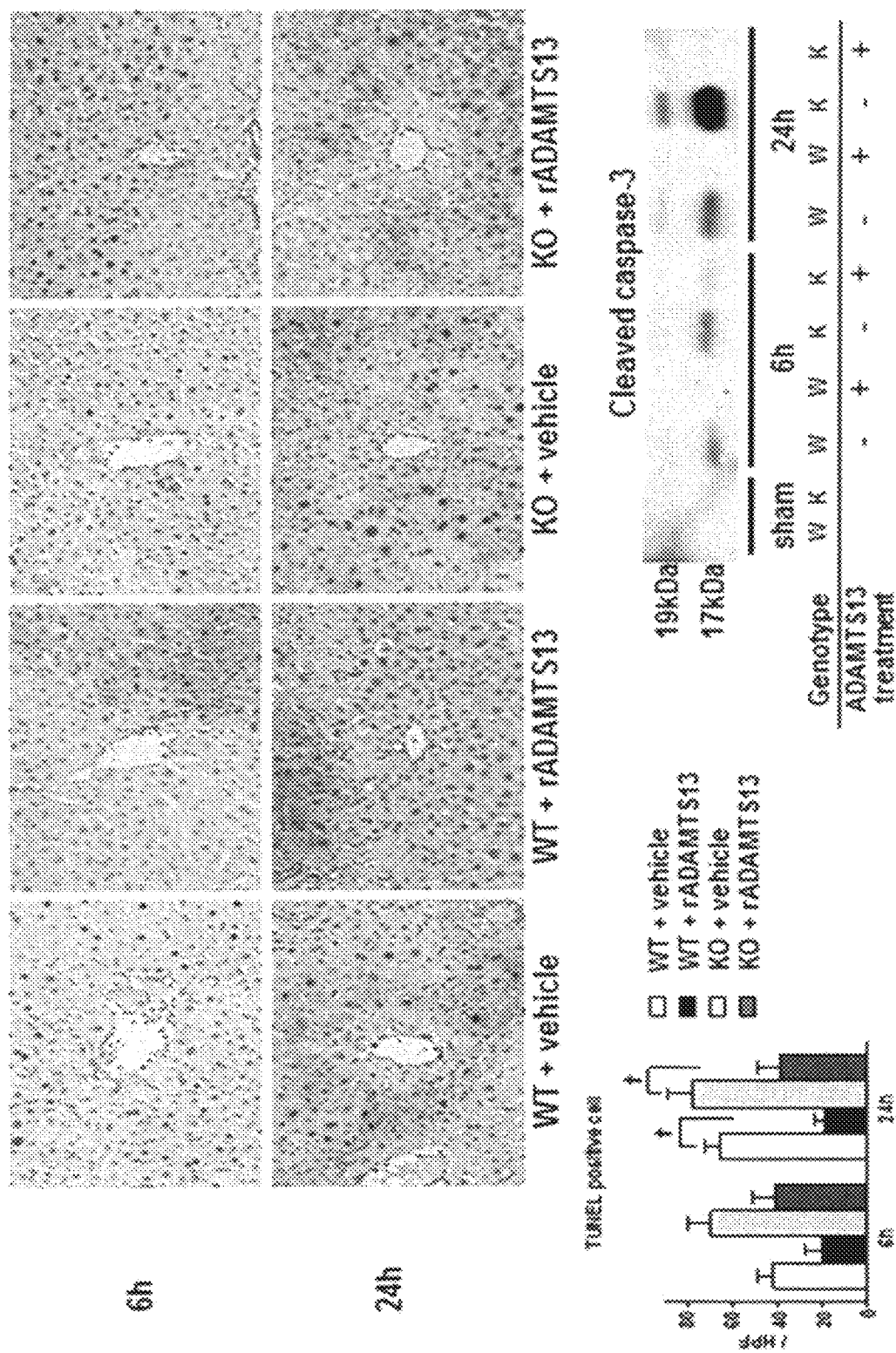

[Fig. 21]
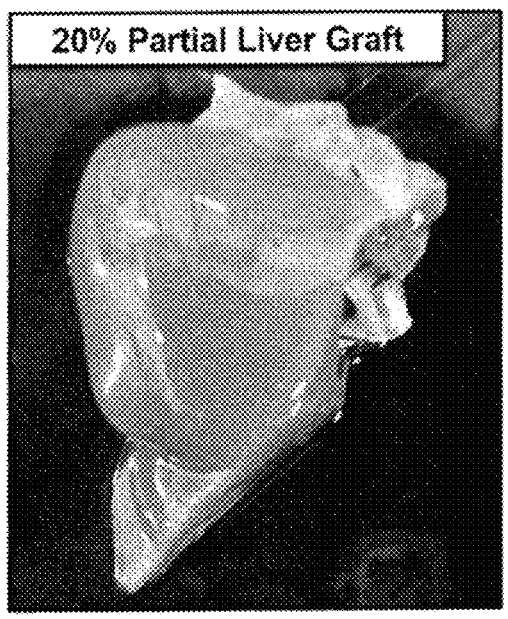
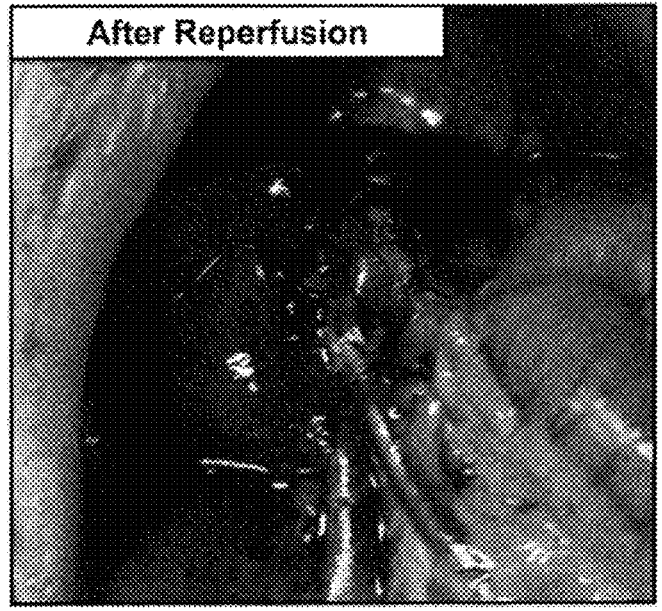

[Fig. 22]
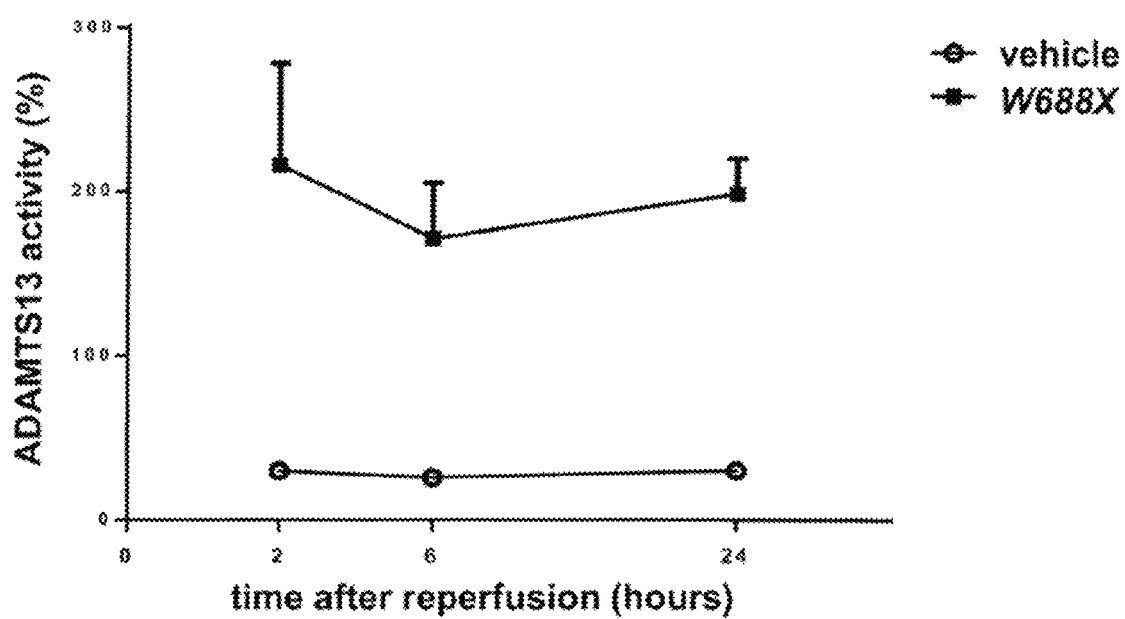

[Fig. 23]
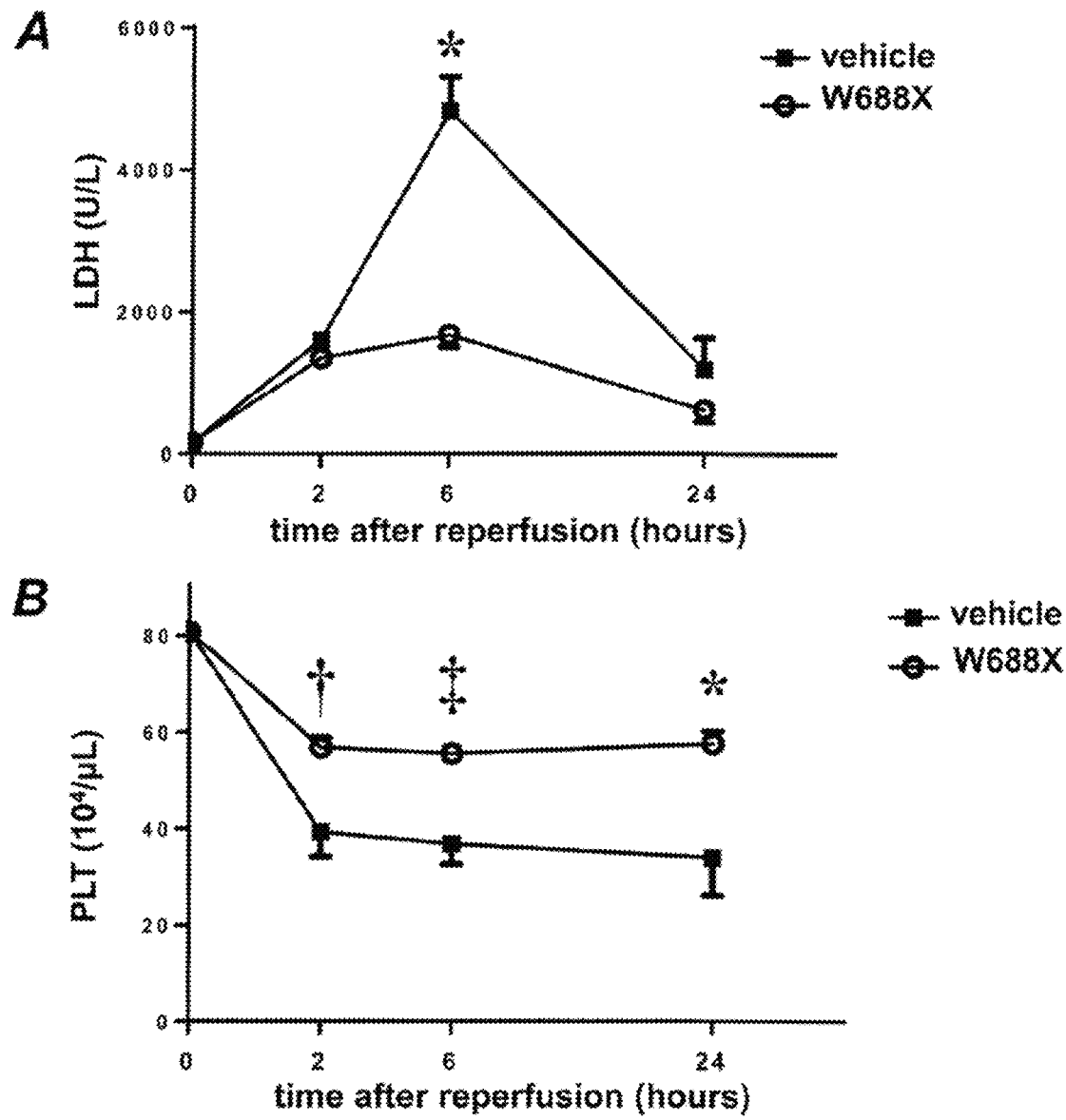

[Fig. 24]
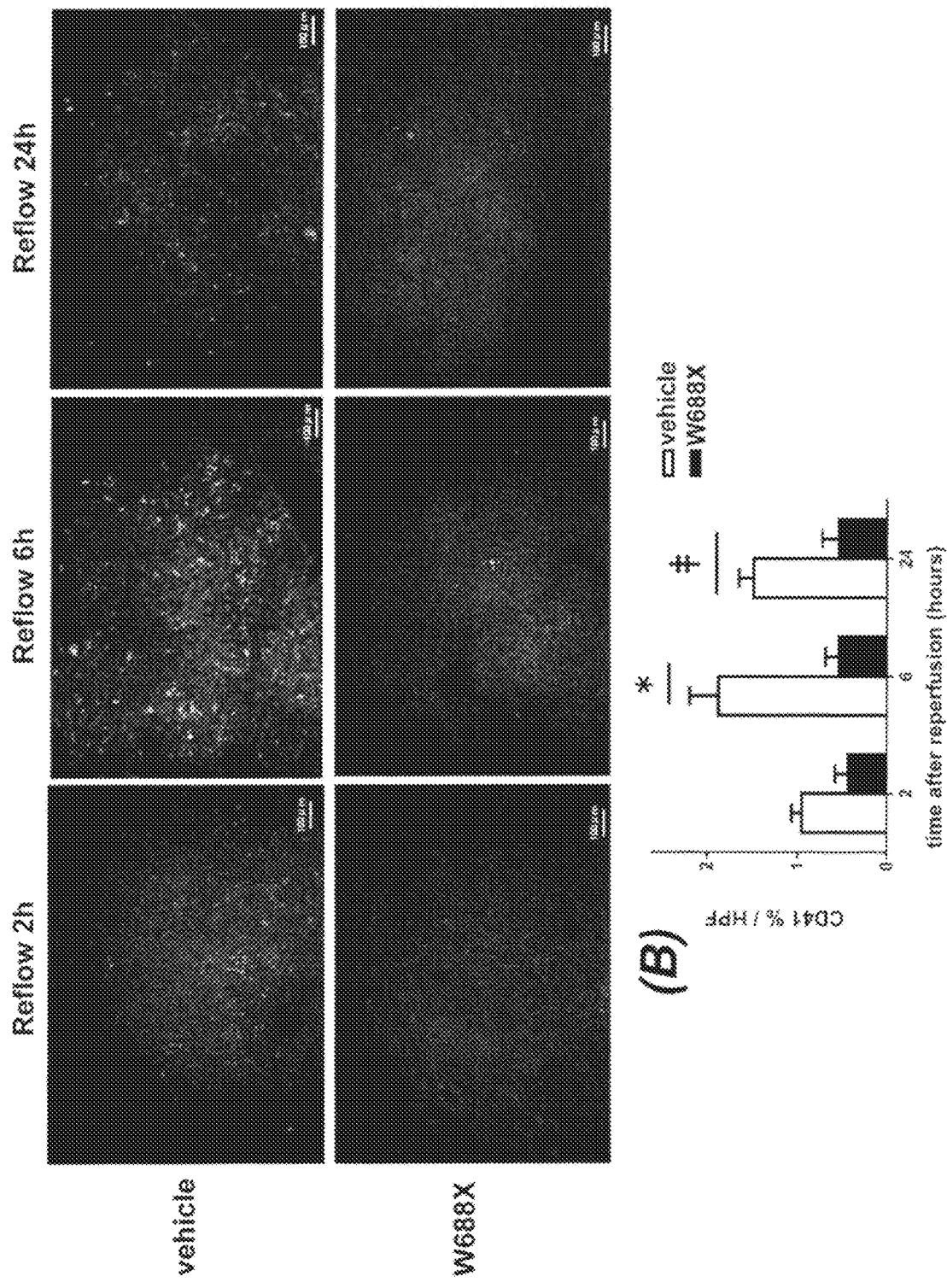

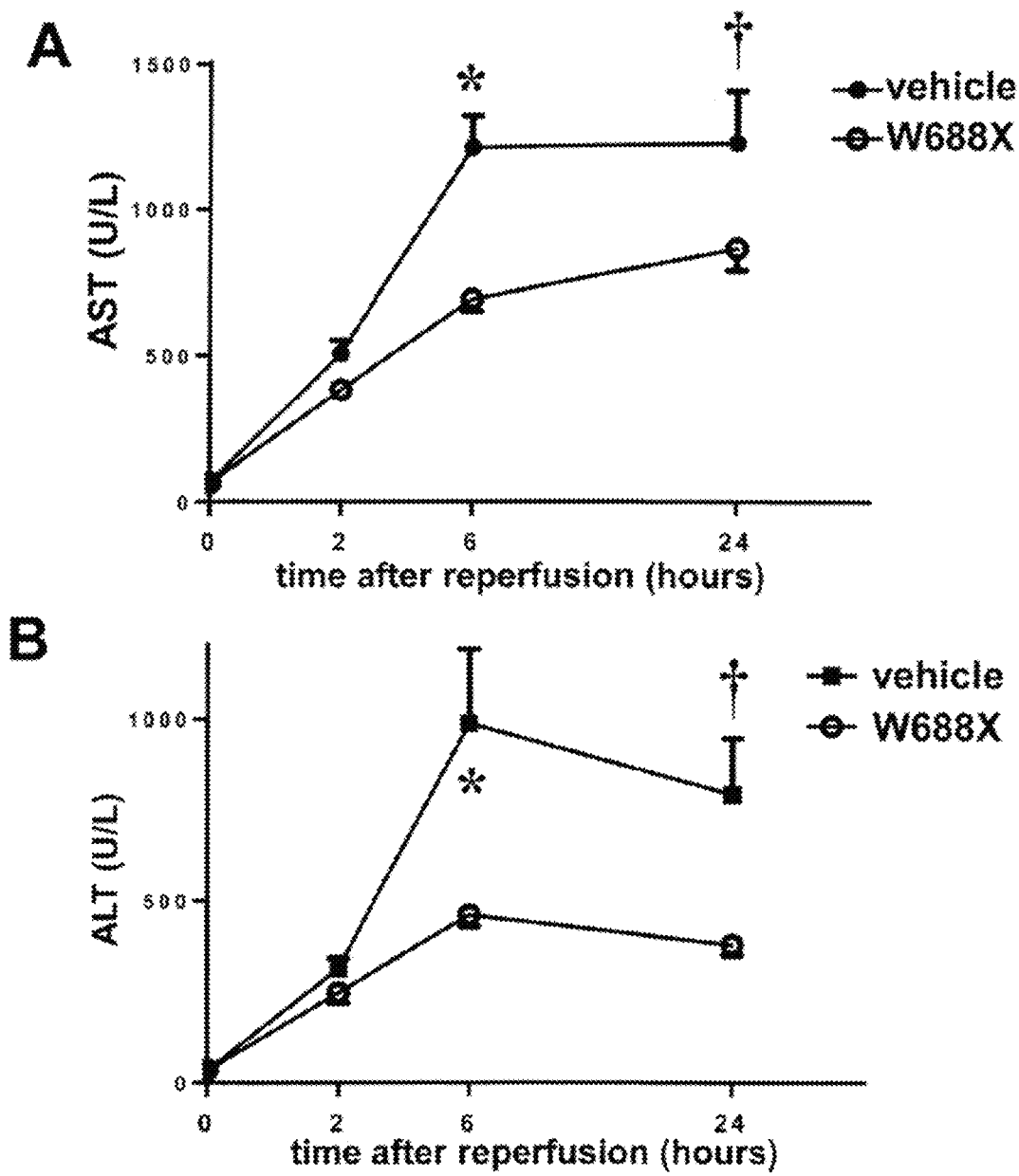
[Fig. 25]

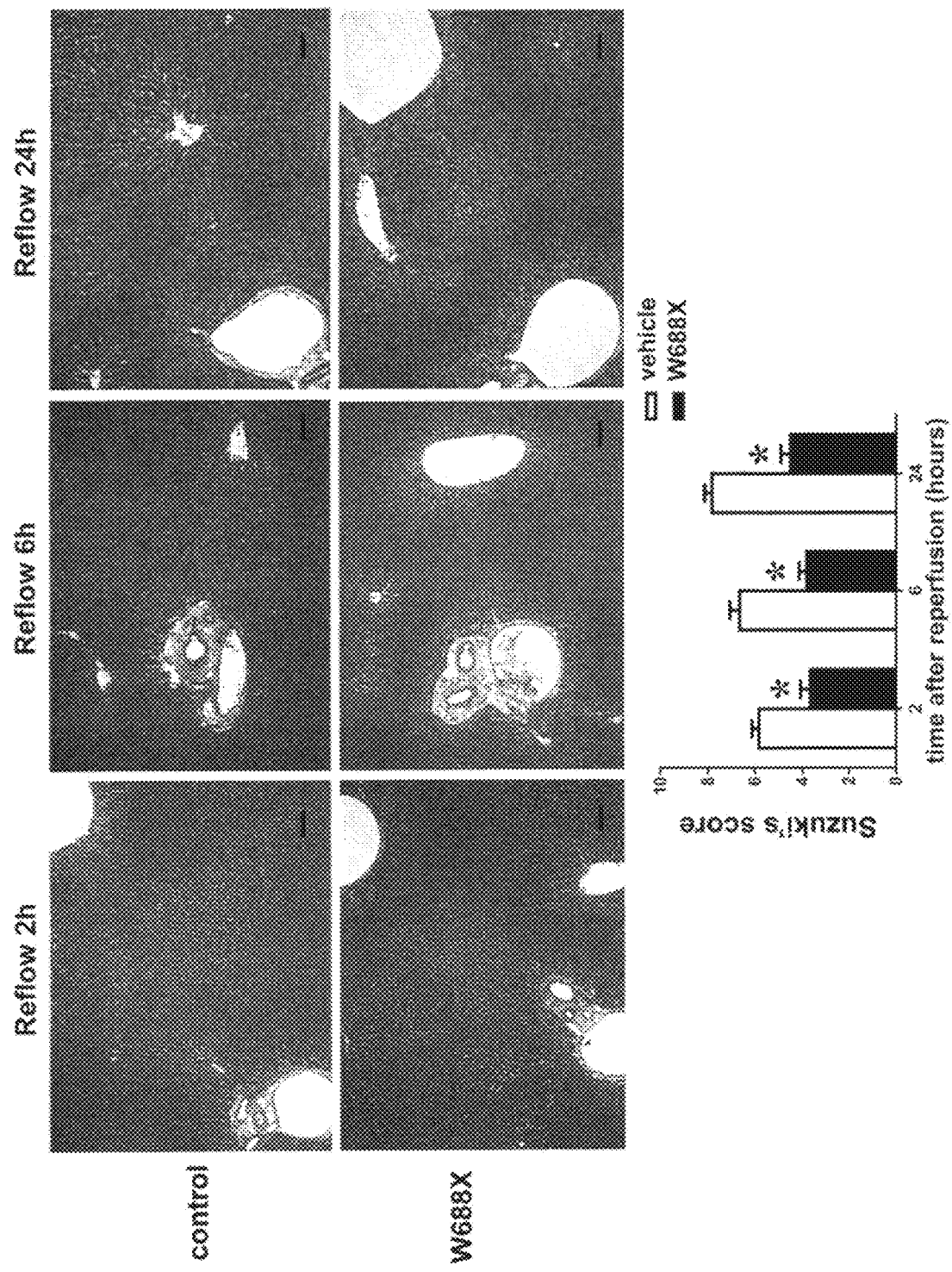
[Fig. 26]

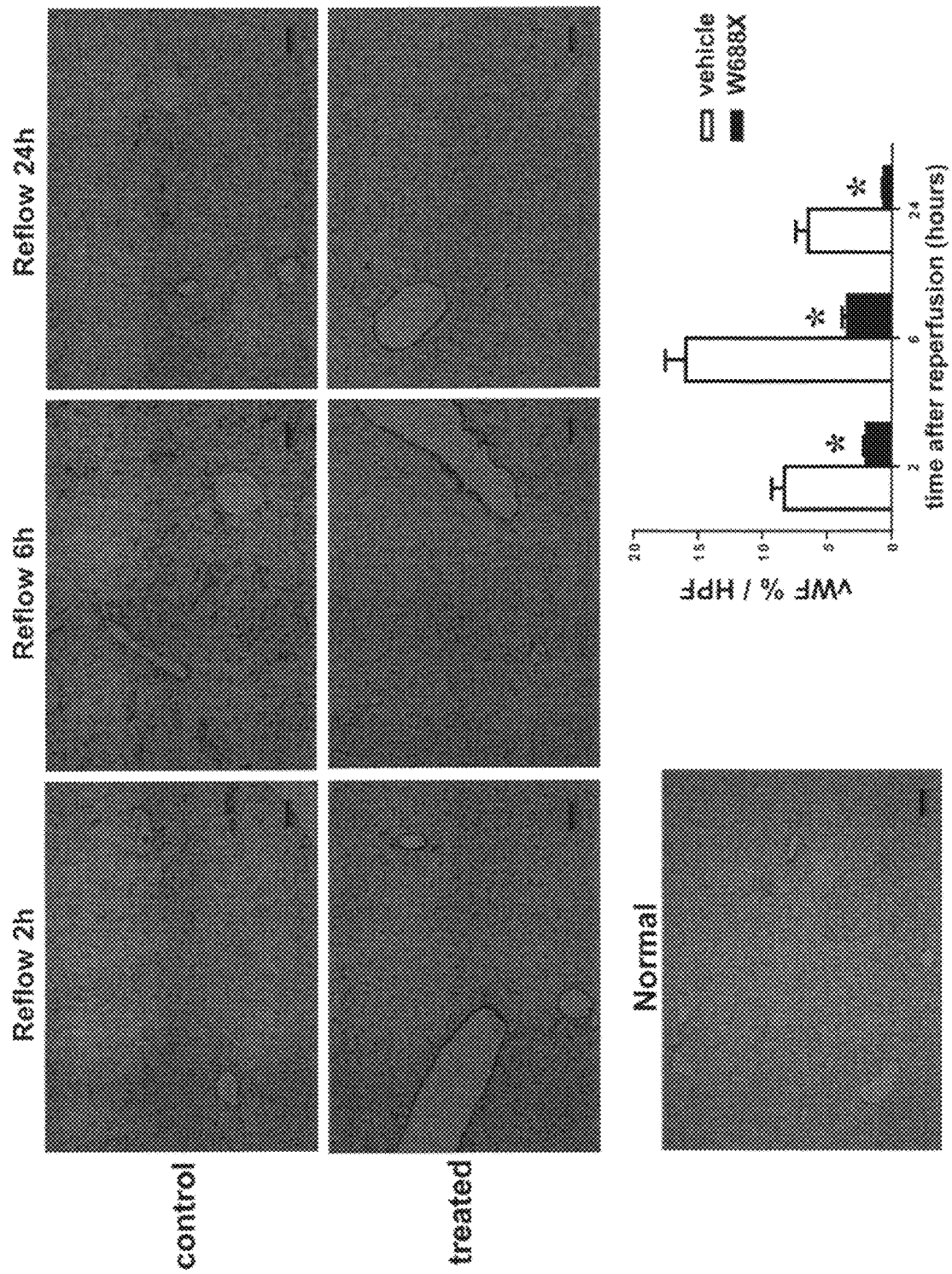
[Fig. 27]

[Fig. 28]
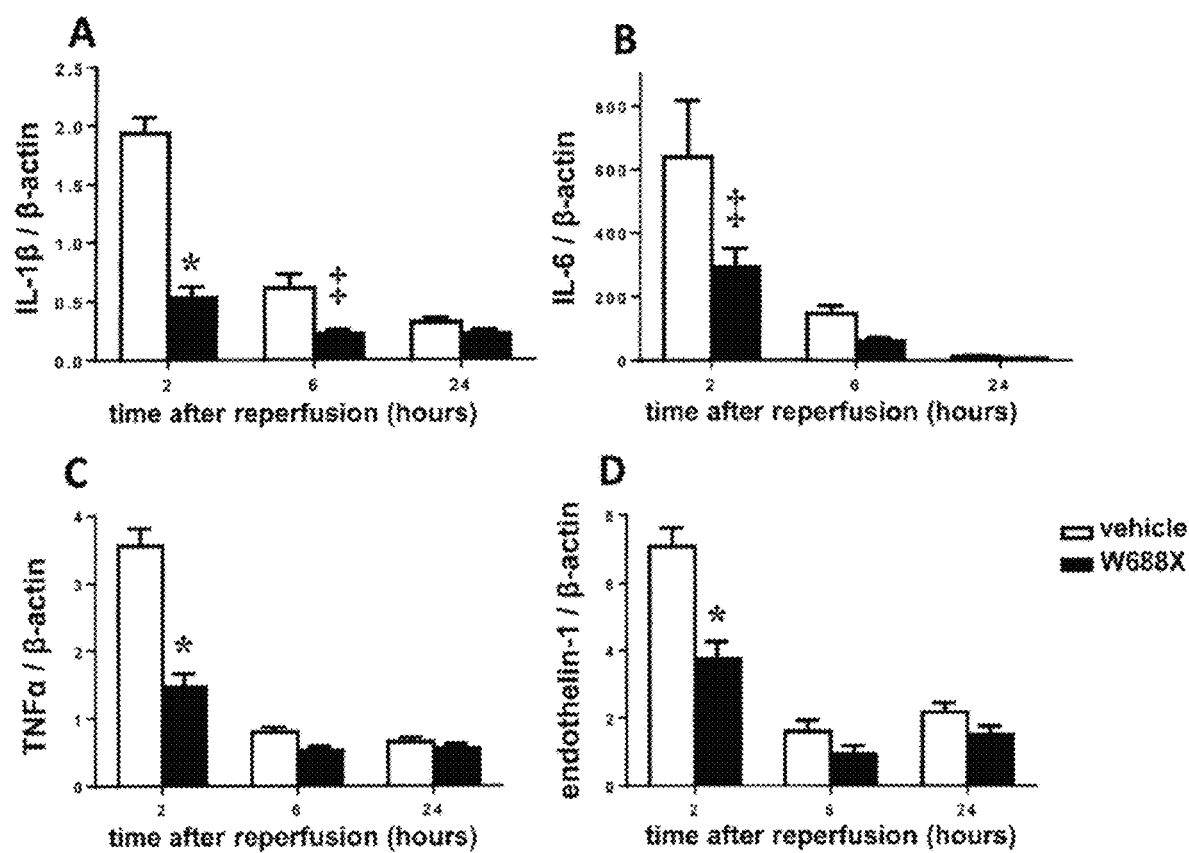

DIAGNOSTIC AGENT AND MEDICINE COMPRISING ADAMTS13 AS MAIN INGREDIENT

TECHNICAL FIELD

The present invention relates to a protein in the field of ethical drug. More specifically, the present invention relates to new use of a whole length or its partial fragment of a specific cleaving enzyme (hereinafter referred to as "ADAMTS13") of von Willebrand Factor (hereinafter also referred to as "vWF") involved in blood coagulation in the clinical field. Specifically, the present invention relates to new use of a whole length or its partial fragment of ADAMTS13 in the field of liver damage, hepatic ischemia/reperfusion injury and liver transplantation.

BACKGROUND ART

The liver is an important organ for controlling metabolism, detoxification (detoxification of alcohol and toxic substances) and body's defense (immunity). Acute hepatitis is a disease exhibiting acute hepatic dysfunction which is mainly caused by infection of hepatitis virus and its symptom includes jaundice, anorexia, nausea and vomiting, systemic sense of fatigue, fever, and the like. Up till the present, five types of hepatitis viruses, types A, B, C, D and E, have been identified. Acute hepatitis is generally a disease with a benign course but becomes fulminant in about 1-2% of its patients, and once being fulminant, the possibility of high-rate death is increased and liver transplantation therapy becomes necessary.

The prodromal symptom of acute hepatitis is a so-called common cold-like symptom (fever, pharyngeal pain and headache) and, at an earlier stage of the disease, it is often diagnosed as common cold and a common cold drug is often prescribed. The diagnosis of acute hepatitis at this stage is difficult. A specific symptom exhibiting the occurrence of liver dysfunction is jaundice, and usually, brown urine is observed several days before the yellowing of the eyeball and the yellowing of the skin appear. The brown urine is urine colored like oolong tea and its color becomes blackened to the color like coca cola with the progress of jaundice. Almost at the same time as the appearance of jaundice, symptoms such as anorexia, systemic sense of fatigue, nausea and vomiting appear.

The diagnosis of acute hepatitis is done, in addition to the above-mentioned subjective symptoms, by examination findings such as a marked increase in hepatocellular enzymes, ALT (GPT) and AST (GOT), and an increase in a bilirubin value which serves as an index of jaundice. The increase in these numerical values indicates that broad hepatocyte damage has occurred. The diagnosis of the causative viruses is carried out by blood test specific to the respective viruses to identify the causative viruses. Namely, IgM HA antibody positive for type A; IgM HBc antibody positive and HBs antigen positive for type B; HCV-RNA positive and HCV antibody positive for type C; IgM HA antibody negative, IgM HBc antibody negative, HCV-RNA negative, anti-nuclear antibody negative (negation of autoimmune hepatitis) and negation of a known viral infection for type Non-ABC.

For diagnosis of severity, severity of liver damage is indicated by blood coagulation test such as a prothrombin time and hepaplastin time, which acutely reflect hepatic spare ability, by a blood test. Although normal acute hepatitis does not show a conscious disorder, when acute hepatitis is fulminant and broad hepatocyte damage occurs, the detoxification function of the liver is deteriorated because the hepatic spare ability markedly decreases. Various toxic substances are not metabolized and eliminated in the liver and remain in the body to cause a brain function disorder to exhibit symptoms such as day-night reversal, delirium, drowsiness, coma, and the like. A conscious disorder caused by a decrease in the hepatic spare ability is called as hepatic coma. Based on an extent of a prothrombin time and a conscious disorder, acute hepatitis is classified into three severities, i.e. a normal type, severe hepatitis and fulminant hepatitis. Once acute hepatitis is fulminant, the possibility of high-rate death increases and liver transplantation therapy becomes necessary.

Acute hepatitis has different course and severity depending on the kind of the causative viruses. Hepatitis A and hepatitis E are transient and not chronic. Hepatitis B is highly chronic when infected with neonatal and pediatric stages but is in principle transient and rarely chronic when infected in adult. Hepatitis C is highly chronic regardless of the age of the infection. A probability that acute hepatitis becomes severe and fulminant leading to death is 1-2% for hepatitis B and non-ABC and 0.5% or less for hepatitis C and A. For hepatitis A, the mortality rate itself is low but, due to its oral infection, secondary infection occurs in a family to cause an explosive epidemic. Recently, infection in an aged person of 50 years or more is increasing which becomes severe, and care should be taken.

Acute hepatitis, except for hepatitis C, is a disease which is transient and is easily naturally healed. The most important observation point for the treatment of acute hepatitis is a determination of whether or not an extreme period has passed. When acute hepatitis is suspected to become severe or fulminant, prompt treatment by a specialist is necessary. The life prognosis of acute hepatitis is extremely good unless it becomes severe and fulminant. For hepatitis A and B, life-long immunity can be established and reinfection would not occur. For hepatitis C, after the lapse of the acute phase, interferon treatment is required for the treatment of the disease which is protracted and chronic.

As a drug therapy, there is not particular need for administration of a drug in most cases but in the acute phase the transfusion is carried out because anorexia and systemic sense of fatigue are often complained. Corticosteroid is a kind of potent anti-inflammatory agents and immunosuppressive agents. Corticosteroid suppresses immune response as an exclusion mechanism of hepatitis virus and possibly make hepatitis protracted and therefore is not administered in normal acute hepatitis. In the case that acute hepatitis becomes possibly severe and fulminant, however, a therapeutic effect can be expected by administering the medicine at a very early stage and suppressing the immune response. Also, in the case where a high degree of jaundice is sustained, corticosteroid may be effective. However, in view of side effects, it should not be easily used and once administration is started, the administration should be carried out in as short period of time as possible.

In the case where acute hepatitis B becomes severe and protracted, the anti-viral agent such as lamivudine and entecavir is administered. The determination of administration and discontinuation of administration of the antiviral agent is conducted by a specialist. In the natural course of acute hepatitis C, about 50-90% of cases are protracted and become chronic. For the prevention of chronicity of acute hepatitis C, interferon (IFN) is administered for 2-6 months. The precautions in the case of IFN administration are the same as those of chronic hepatitis and the treatment is performed under the management of a specialist in view of various side effects.

In the liver, blood flowing through the portal vein and the artery is mixed in the net-like sinusoid, corresponding to the capillary of body circulation, and flows out to the liver vein. In the liver, the terminal of the portal vein (terminal portal vein branch) and the terminal of the liver artery form the sinusoid, which flows into the center vein (terminal liver vein). As in the capillary system of body circulation, the sinusoid participates in the exchange of various substances (nutrients, ammonia, etc.) as the hepatic microcirculation system.

Thrombotic microangiopathy (TMA) is one of life threatening diseases characterized by platelet coagulation in the whole body, and therefore multi-organ failure. A famous syndrome belonging to the category of TMA includes thrombotic thrombocytopenic purpura (TTP) accompanied by the five symptoms (platelet reduction, microangiopathic hemolytic anemia, fever, renal dysfunction, psychoneurotic disorder) and hemolytic uremic syndrome (HUS) accompanied by the three symptoms (platelet reduction, microangiopathic hemolytic anemia, acute renal failure), as firstly reported by Moschcowitz in 1924. Since there are many cases where these typical symptoms are not manifested and these two diseases are difficult to distinguish from each other, they are often referred to as TTP/HUS or taken together as TMA.

TMA most frequently develops after enteritis by the enterohemorrhagic *E. coli* such as 0157 or 0111 but also caused by a drug, bone marrow transplantation and liver transplantation. Abnormality of ADAMTS13 is considered to be another cause of TMA. ADAMTS13 is a protein cleavage enzyme belonging to a group of metalloproteases and cleaves only vWF, which relates to hemostasis. vWF is originally produced as a large mass of UL-vWFM (unusually large-vWF multimer) in vascular endothelial cells, which is then finely cleaved by ADAMTS13 to obtain vWF in an appropriate size to thereby exhibit an appropriate hemostatic effect. However, if the function of ADAMTS13 is extremely reduced, vWF in an inappropriately large size remains to exert an excessive hemostatic effect, leading to generation of platelet thrombus in the blood vessel. As the thrombus by vWF is more likely to be generated with thinner blood vessels, it is considered that platelet thrombus is generated in the microvessels to develop TMA.

It is known that TMA caused by the decrease in the activity of ADAMTS13 is characterized by that (1) the renal dysfunction is relatively light and that it leads to thrombotic thrombocytopenic purpura (TTP) accompanied by (2) severe fever and (3) severe psychoneurotic disorder. These symptoms taken together with (4) platelet reduction and (5) hemolytic anemia are referred to as five symptoms. It is reported however that all these symptoms are observed together only in about 30% of cases.

The causes to greatly reduce the activity of ADAMTS13 include congenital gene abnormality and acquired factors. A disease that develops TMA due to congenital gene abnormality of ADAMTS13 is called Upshaw-Schulman syndrome. This is a rare disease accompanied by severe jaundice and platelet reduction from the newborn time. For the cause of acquired reduction of the ADAMTS13 activity, an autoantibody (IgG type) to ADAMTS13 is the most important. The disease with unknown cause is idiopathic and the disease developed by other diseases is secondary. The disease is developed widely from an infant to an elderly person. A male-to-female ratio is said to be 1:2, a little dominant in female. Morbidity is reported to be about 4 per one million but due to improved diagnostic technology in recent years higher morbidity is assumed.

Although the measurement of the ADAMTS13 activity is useful for assessing the disease progress of TMA, it should be noted that TMA cannot be excluded by this test alone since no decrease in the ADAMTS13 activity is often observed. The name of thrombotic thrombocytopenic purpura (TTP) is registered as a subject in the field of clinical research and study in the state project to overcome refractory diseases.

Standard therapy for typical TMA is plasma exchange (PE) at an early stage, and the healing rate in Japan is now up to 90%. However, the mortality of TMA after liver transplantation is still very high.

The mechanism of TTP is considered to be that an ultra-large molecular weight vWF multimer (UL-VWFM) produced from endothelial cells is not cleaved when the ADAMTS13 activity is reduced to lead to excessive platelet aggregation and thrombus formation in a portion where a high shear stress occurs such as small blood vessels (Blood, 2008; 112: 11-18 (Non-patent reference 1)).

The problem in TTP treatment includes (1) although the diagnosis of TTP/HUS is relatively easy in clinical diagnosis and HUS can be excluded (specificity 90%) if severe deficiency (<5%) of ADAMTS13 is observed, the sensitivity of test is indistinct; (2) for some causes of TTP/HUS, plasma exchange is not effective (J Clin Apher 2012; 27: 112-116 (Non-patent reference 2)); and (3) the recurrence rate of the acquired TTP is still as high as 20-500.

The usefulness of plasma exchange in the idiopathic TTP is established. TTP is problematic in its recurrence rate. In recent years, the possibility is being suggested that the recurrence rate can be reduced by the use of Rituximab (Br J Haematol 2012; 158: 323-335 (Non-patent reference 3)). On the other hand, for TTP caused after bone marrow stem cell transplantation or TTP associated with malignant tumor, there is no usefulness of plasma exchange (treatment of the primary disease).

Ischemic reperfusion injury is caused by production of various toxic substances in microcirculation in the organs or tissues where the organs or the tissues are in an ischemic state and blood reperfusion occurs. Ischemia/reperfusion theory reported by McCord is the first (McCord, N Engl J Med 1985; 312: 159 (Non-patent reference 4)). The degree of injury may vary depending on the duration and degree of ischemia, the kind of the organ, and the like. Injury is sometimes severe in the case of incomplete ischemia. It is thought that reperfusion causes vascular endothelial cell injury and microcirculation injury to lead to organ damage. A mechanism to cause injury includes injury caused by production of free radicals such as active oxygen such as super oxide (02-) and hydroxyl radical (HO•) and nitrogen monoxide (NO), injury caused by production of various chemical mediators such as various cytokines, endothelin and arachidonic acid, and injury caused by interaction between activated neutrophils and vascular endothelial cells. Injury is caused not only locally but also secondarily in the main organs of the whole body (remote organ damage). In particular, the brain, lung, liver, kidney, and the like are targeted, resulting in multi-organ failure. It is often observed after reperfusion therapy to myocardial infarction, cerebral infarction, inter-intestinal membrane vascular occlusion, and the like or after organ transplantation.

Liver failure is a group of diseases that exhibit jaundice, ascites, hepatic encephalopathy, bleeding tendency, and the like due to decreased number and decreased function of hepatocytes and is classified into acute and chronic liver failure based on their course. Acute liver failure is normally limited to the disease where necrosis and inflammation occur in the normal liver and liver failure occurs within six months. Its typical disease is fulminant hepatitis which is characterized by massive or submassive hepatic necrosis from histopathological point of view, exhibits systemic inflammatory response syndrome (SIRS) with intercurrent multiple organ failure (MOF) and often results in poor prognosis.

With the liver in the state of liver failure in which no likelihood of function recovery by any medical treatment remains due to various diseases, the basic functions of the body cannot be maintained unless it is replaced with the healthy liver provided, liver transplantation is performed. An adaptation disease of liver transplantation includes, in an adult, liver cirrhosis (cirrhosis type B, cirrhosis type C, alcoholic liver cirrhosis, autoimmune cirrhosis, non-B non-C liver cirrhosis), cholestatic diseases (primary biliary cirrhosis (PBC), primary sclerosing cholangitis (PSC), Byler disease, Caroli disease, biliary atresia (BA)), fulminant hepatitis, metabolic diseases (hemochromatosis, etc.), liver tumor (liver cancer (primary, metastatic), benign tumor), and the like.

On the other hand, in an infant, an adaptation disease of liver transplantation includes cholestatic diseases (biliary atresia, Alagille syndrome, Byler disease, cystic dilatation of common bile duct, Caroli disease, etc.), liver cirrhosis (autoimmune hepatitis, etc.), metabolic diseases (a-1 antitrypsin deficiency, etc.), neonatal hepatitis, fulminant hepatitis, liver tumor (hepatoblastoma, hepatocellular carcinoma, etc.), and the like.

For liver transplantation, the liver to be transplanted taken from a donor, after being arranged outside the body in a shape for transplantation, is stored in a cold storage solution until it is implanted.

ADAMTS13 (a disintegrin-like and metalloproteinase with thrombospondin type 1 motifs 13), which is a specific cleavage enzyme of a hemostatic factor von Willebrand (vWF), was found 13th as a zinc-type metalloprotease belonging to ADAMTS family in 2001.

vWF has a structure in which single subunits consisting of 2050 amino acid residues are linked via disulfide bond in a manner of N-terminus to N-terminus or C-terminus to C-terminus, has a unique high molecular weight structure and produced as unusually-large vWF multimer (UL-VWFM). ADAMTS13 specifically cleaves Ty842-Met843 (Tyr1605-Met1606 as cDNA indication) bonding of vWF subunits to reduce a size of molecular weight of vWF to thereby prevent an excess platelet aggregation caused by UL-VWFM, allowing for adjustment of "being suitable for formation of hemostatic thrombus but preventing pathologic formation of thrombus".

ADAMTS13 was first identified as a key enzyme causing refractory blood disease, thrombotic thrombocytopenic purpura (TTP). However, it is clarified that "microcirculatory injury by platelet thrombosis" caused by failure of ADAMTS13/vWF (enzyme/substrate) balance, which was found in elucidation of pathologic conditions of the disease, forms the basic pathology of various diseases.

The ADAMTS13 gene is in the chromosome 9q34. Its cDNA consists of 29 exons, consisting of 4281 bp from the initiation codon to the stop codon. ADAMTS13 is a large protein consisting of 1427 amino acid residues. ADAMTS13 contains 10 Asn-binding sugar chains in the molecule and has a total of 190 kD of the molecular weight. Its primary structure, starting from the N-terminus, consists of signal peptide (S), propeptide (P), reprolysin-type metalloprotease domain (MP), disintegrin-like domain (D), thrombospondin type-1 (Tsp1) motif (T1-8), cysteine-rich domain (C), spacer domain (Sp), again repeat of Tsp1 motif, and two CUB domains at the C-terminus. Asn-binding sugar chain of the enzyme is considered to be important in secretory function of the cell. The liver was first identified as the organs producing ADAMTS13 and the hepatic stellate cells (previously Itoh cells) were identified as the cells producing ADAMTS13. The hepatic stellate cells are indicated to be closely related to the progress of hepatic cirrhosis through transformation to the fibroblast cells. From this, the decrease in the ADAMTS13 activity associated with development of liver cirrhosis was shown (Uemura M, Fujimura Y, Matsumoto M, et al: Comprehensive analysis of ADAMTS13 in patients with liver cirrhosis. Thromb Haemost 2008; 99: 1019-1029 (Non-patent reference 5)). The enzyme is also reported to be present in platelets, vascular endothelial cells, and podocyte of the kidney.

The significance of production of the enzyme in these organs and the cells is not clarified. However, the liver is considered to be the most important organ for maintaining the blood level of ADAMTS13 (Yoshihiro Fujimura, The Journal of Japanese College of Angiology Vol. 51 No. 3, 2011 (non-patent reference 6). The reasons for this include the following two: (1) terminally ill patients suffering from biliary cirrhosis due to congenital biliary atresia have the ADAMT13 activity in blood reduced to 20-30% and exhibit three pathological symptoms of thrombotic microangiopathy (TMA), i.e. hemolytic anemia, platelet reduction and renal dysfunction but, when receiving living donor liver transplantation and engraftment, the TMA findings are no longer observed (Matsumoto M, Chisuwa H, Nakazawa Y, et al: Liver transplantation rescues a deficient state of von Willebrand factor cleaving protease activity in patients with liver cirrhosis due to congenital biliary atresia. Blood 2000: 96: 636a (abstract) (Non-patent reference 7)); (2) the severity of the clinical symptom of adult patients with cirrhosis mainly due to hepatitis C is parallel to the ADAMTS13 activity in blood and, at a terminal stage, the activity is lowered to 20-30% (Uemura M, Tatsumi K, Matsumoto M, et al: Localization of ADAMTS13 to the stellate cells of human liver. Blood 2005; 106: 922-924 (non-patent document 8)).

In 2008, Chauhan et al. reported the results that ADAMTS13 downregulated both thrombus and inflammation (Chauhan A K, Kisucka J, Brill A, et al: ADAMTS13: a new link between thrombosis and inflammation. J Exp Med 2008; 205: 2065-2074 (Non-patent reference 9)). As such, ADAMTS13 is shown to have an antithrombotic activity and an anti-inflammatory activity and thus is expected as a therapeutic agent for cerebral infarction. Namely, Zhao et al. (Zhao B Q, Chauhan A K, Canault M, et al: von Willebrand factor-cleaving protease ADAMTS13 reduces ischemic brain injury in experimental stroke. Blood 2009; 114: 3329-3334 (Non-patent reference 10)) and Fujioka et al. (Fujioka M, Hayakawa K, Mishima K, et al: ADAMTS13 gene deletion aggravates ischemic brain damage: a possible neuroprotective role of ADAMTS13 by ameliorating postischemic hypoperfusion. Blood 2010; 115: 1650-1653 (Non-patent reference 11) conducted a cerebral ischemia reperfusion experiment in a mouse middle cerebral artery occlusion model to artificially create cerebral infarction and calculated a cerebral infarction volume to find that ADAMT13 knockout mice significantly increased the cerebral infarction volume as compared to that of wild type mice (Non-patent reference 10). The tissue observation of the cerebral infarction part confirmed that the knockout mouse group had a large number of microthrombus and a lot of infiltration of inflammatory cells. The thrombus was shown to be the one rich in vWF. The cause that the knockout mice exhibited a larger range of cerebral infarction was considered to be platelet thrombus containing a large amount of vWF and an excessive infiltration of white blood cells. Further, it was also reported that administration of gene expression-based human ADAMTS13 preparation immediately before reperfusion to wild type mice significantly reduced the range of cerebral infarction (Non-patent reference 11). As described above, from the results obtained by the experiment with mice, the possibility of an ADAMTS13 formulation as a medicament for treatment and prophylaxis of cerebral infarction is shown.

Loss of the ADAMTS13 activity is associated with a number of conditions, for example, TTP (Moake J L, Semin Hematol.2004 January; 41(1): 4-14 (Non-patent reference 12)), acute and chronic inflammation (Chauhan et al., J Exp Med. 2008 Sep 1; 205(9): 2065-74 (Non-patent document 9)), and most recently, severe *falciparum* malaria parasite (*Plasmodium falciparum*) malaria (Larkin et al., PLoS Pathog.2009 March; 5(3): e1000349 (Non-patent reference 14)).

The ADAMTS13 formulation has been used for disorders associated with the formation and/or presence of one or more thrombus. Examples of disorders associated with the formation and/or presence of one or more thrombus include hereditary thrombotic thrombocytopenic purpura (TTP), acquired TTP, arterial thrombosis, acute myocardial infarction (AMI), stroke, sepsis and disseminated intravascular clotting (DIC).

The ADAMTS13 formulation has also been used for treatment or prevention of infarction. Examples of infarction include myocardial infarction (heart attack), pulmonary embolism, cerebrovascular event such as stroke, peripheral arterial occlusion diseases (gangrene, etc.), antiphospholipid syndrome, sepsis, giant cell arteritis (GCA), hernia and intestinal volvulus.

WO 2005/062054 pamphlet (Patent reference 1) discloses a method of detecting the degree of thrombophilia or thrombosis by measuring ADAMTS13. It discloses that thrombosis includes acute or chronic myelogenous leukemia, acute premyelocytic leukemia, systemic lupus erythematosus, pulmonary embolism, cerebral infarction, hepatic veno-occlusive disease, acute lymphocytic leukemia, thrombotic microangiopathy, thrombotic thrombocytopenic purpura, hemolytic-uremic syndrome and deep vein thrombosis. Also, WO 2006/049300 pamphlet (Patent reference 2) discloses a method of detecting platelet thrombosis or organ disorder in a patient with DIC or systemic inflammatory response syndrome (SIRS) by analyzing ADAMTS13 and/ or its degradation factor (e.g. elastase, plasmin and thrombin).

JP 2007/088849 (Patent reference 3) discloses a method of grasping DIC conditions by analyzing an amount and/or an enzymatic activity of ADAMTS13 in a patient with disseminated intravascular clotting (DIC).

JP 2009-539757 (Patent reference 4) discloses a pharmaceutical composition comprising a pharmaceutically effective amount of ADAMTS13 having thrombolytic activity.

JP 2010-280571 (Patent reference 5) discloses a method of using ADAMTS13 family protein as a cell aid for enhancing the graft survival rate of graft cells, a cell transplantation supplement comprising said protein as an effective ingredient, and a method of preparing graft cells comprising a step of adding said protein.

JP 2013-505270 (Patent reference 6) discloses a ADAMTS13 formulation which is suitable for drug administration and can be stored for a long period of time without loss of the activity or excess coagulation.

Up till the present, relationship of ADAMTS13 with acute and chronic liver damage, hepatic ischemia reperfusion injury, liver transplantation, and acute liver failure/fulminant hepatitis has scarcely been clarified and it was not known to use ADAMTS13 as a therapeutic agent for these diseases.

PRIOR ART

Patent Reference

Patent reference 1: WO 2005/062054 pamphlet
Patent reference 2: WO 2006/049300 pamphlet
Patent reference 3: JP 2007/088849
Patent reference 4: JP 2009-539757
Patent reference 5: JP 2010-280571
Patent reference 6: JP 2013-505270

Non-Patent Reference

Non-patent reference 1: Blood, 2008; 112: 11-18
Non-patent reference 2: J Clin Apher 2012; 27: 112-116
Non-patent reference 3: Br J Haematol 2012; 158: 323-335
Non-patent reference 4: McCord, N Engl J Med 1985; 312: 159
Non-patent reference 5: Uemura M, Fujimura Y, Matsumoto M, et al: Comprehensive analysis of ADAMTS13 in patients with liver cirrhosis. Thromb Haemost 2008; 99: 1019-1029
Non-patent reference 6: Yoshihiro Fujimura, The Journal of Japanese College of Angiology Vol. 51 No. 3, 2011
Non-patent reference 7: Matsumoto M, Chisuwa H, Nakazawa Y, et al: Liver transplantation rescues a deficient state of von Willebrand factorcleaving protease activity in patients with liver cirrhosis due to congenital biliary atresia. Blood 2000: 96: 636a (abstract))
Non-patent reference 8: Uemura M, Tatsumi K, Matsumoto M, et al: Localization of ADAMTS13 to the stellate cells of human liver. Blood 2005; 106: 922-924
Non-patent reference 9: Chauhan A K, Kisucka J, Brill A, et al: ADAMTS13: a new link between thrombosis and inflammation. J Exp Med 2008; 205: 2065-2074
Non-patent reference 10: Zhao B Q, Chauhan A K, Canault M, et al: von Willebrand factor-cleaving protease ADAMTS13 reduces ischemic brain injury in experimental stroke. Blood 2009; 114: 3329-3334
Non-patent reference 11: Fujioka M, Hayakawa K, Mishima K, et al: ADAMTS13 gene deletion aggravates ischemic brain damage: a possible neuroprotective role of ADAMTS13 by ameliorating postischemic hypoperfusion. Blood 2010; 115: 1650-1653
Non-patent reference 12: Moake J L, Semin Hematol.2004 January; 41(1): 4-14
Non-patent reference 14: Larkin et al., PLoS Pathog.2009 March; 5(3): e1000349

DISCLOSURE OF THE INVENTION

Technical Problem to be Solved by the Invention

The liver is an extremely important organ that controls important functions of a human body. There is still a need for an effective therapeutic agent and a diagnostic agent for acute and chronic liver damage, hepatic ischemia reperfusion injury, hepatic dysfunction in liver transplantation and acute liver failure/fulminant hepatitis.

Means for Solving the Problems

In a liver surgery including liver resection and liver implantation, excluding the factor of tumor, the maximum factor that defines the operative procedure is (residual) liver function and the hepatic spare ability. Liver function in modern medical treatment is just the function of hepatocytes. The liver includes parenchymal cells (hepatocytes: about 60%) and non-parenchymal cells (sinusoidal cells constituting the sinusoidal wall of the liver; vascular endothelial cells other than hepatocytes, Kupffer cells, stellate cells, and the like: about 40%). Up till the present, it has been scarce that the function of the hepatic non-parenchymal cells is assessed in the liver surgery or in the treatment of many acute and chronic liver diseases and the treatment policy is determined on the basis of the results obtained.

The present inventors focused on the hepatic non-parenchymal cells which have not been heretofore considered and found that acute and chronic liver disease can be evaluated by evaluating the function of the hepatic non-parenchymal cells and the treatment policy can be determined. In particular, the present inventors focused on the stellate cells, one of hepatic non-parenchymal cells, and analyzed a protein produced by said cells, ADAMTS13, for the function and expression to find diagnostic significance of ADAMTS13 as a marker of "the function of hepatic non-parenchymal cells" and also a drastic therapeutic effect of a gene recombinant formulation of ADAMTS13 in a non-clinical test.

The present inventors have also found that ADAMTS13 exerts a significant therapeutic effect in various liver diseases such as hepatic ischemia/reperfusion injury, liver dysfunction after liver transplantation, acute liver failure and fulminant hepatitis to complete the present invention.

Thus, the present invention includes the followings.

[1] Use of ADAMTS13 as a biomarker for monitoring the following (1) to (4):

(1) grasping conditions of liver damage, in particular, disorder of hepatic non-parenchymal cells;

(2) hepatic ischemia/reperfusion injury;

(3) index of the liver function after liver transplantation, in particular, the function of hepatic non-parenchymal cells; or (4) acute liver failure/fulminant hepatitis.

[2] Use of [1] above wherein the liver damage is the one after chemotherapy of colorectal cancer.

[3] A method of the following (1) to (4) which comprises measuring or monitoring the ADAMTS13 activity in a sample from a mammal:

(1) a method of testing liver damage, in particular, a disorder of hepatic non-parenchymal cells;

(2) a method of testing hepatic ischemia/reperfusion injury;

(3) a method of testing the liver function after liver transplantation, in particular, the function of hepatic non-parenchymal cells; or (4) a method of testing acute liver failure/fulminant hepatitis.

[4] The method of [3] above wherein the liver damage is the one after chemotherapy of colorectal cancer.

[5] A kit for monitoring of the following (1) to (4) which comprises a means for measuring the ADAMTS13 activity in a sample from a mammal:

(1) a kit for monitoring the onset of liver damage;

(2) a kit for monitoring hepatic ischemia/reperfusion injury;

(3) a kit for monitoring the liver function after liver transplantation; or (4) a kit for monitoring acute liver failure/fulminant hepatitis.

[6] The kit of [5] above wherein the liver damage is the one after chemotherapy of colorectal cancer.

[7] The use, the method or the kit of any one of [3] to [6] above wherein the mammal is human.

[8] A pharmaceutical composition comprising ADAMTS13 or a mutant of ADAMTS13 as an effective ingredient.

[9] An agent for treating diseases selected from the group consisting of liver damage, hepatic ischemia/reperfusion injury, hepatic dysfunction after liver transplantation and acute liver failure/fulminant hepatitis, which comprises ADAMTS13 or a mutant of ADAMTS13 as an effective ingredient.

[10] The pharmaceutical composition or the agent of [8] or [9] above wherein the mutant of ADAMTS13 is a molecule comprising minimum unit necessary for exerting the ADAMTS13 activity consisting of from a metalloprotease domain to a spacer domain.

[11] The pharmaceutical composition or the agent of [10] above wherein the mutant of ADAMTS13 is a C-terminus deficient mutant W688X ("ADAMTS13W688X protein") which is a resultant of deletion of the C-terminal portion from the amino acid at position 689 from ADAMTS13 consisting of 1427 amino acid residues.

[12] A method for diagnosing diseases selected from the group consisting of liver damage, hepatic ischemia/reperfusion injury, hepatic dysfunction after liver transplantation and acute liver failure/fulminant hepatitis in a mammal, which comprises screening the decrease in the ADAMTS13 activity in the hepatic non-parenchymal cells of a mammal.

Effects of the Invention

The present invention relates to new use of a whole length or its partial fragment of ADAMTS13. By using ADAMTS13 in accordance with the present invention, it becomes possible to diagnose quickly and accurately acute and chronic liver damage and to provide an agent for effectively treating liver damage, hepatic ischemia/reperfusion injury, hepatic dysfunction after liver transplantation and acute liver failure/fulminant hepatitis.

BRIEF DESCRIPTION OF DRAWINGS

Although the hepatic spare ability is expected to be sufficiently high in view of the function of hepatocytes, there is also a pathological condition in which liver failure is caused after liver resection due to the extreme decrease in the non-parenchymal cell function. As an example.

FIG. 10A is a graph showing the results of quantitative RT-PCR showing that both the marked increase of the vWF activity and the marked decrease of the ADAMTS13 activity occur by hepatic ischemia and reperfusion.

FIG. 10B is a graph showing that the ADAMTS13 activity in blood decreases by around 30% by ischemia and reperfusion of 70% partial liver and no recovery is observed after 24 hours.

FIG. 11 is a graph showing the ADAMTS13 activity in plasma after reperfusion (A) and the platelet count in peripheral blood after IRI (B) in four experimental groups. It was proved that the platelet count in peripheral blood was proportional to the ADAMTS13 activity in plasma (the higher the ADAMTS13 activity in blood, the more the platelet count in peripheral blood is maintained).

FIG. 12 is a photograph showing the CD42B fluorescence immunostaining of liver tissue after hepatic ischemia and reperfusion (the platelets in the liver tissue are densely red-stained with fluorescence). It is shown that a lot of platelet coagulation occurs in the liver of ADAMTS13 knockout mice as compared to that of wild-type mice but the platelet coagulation in the liver is markedly ameliorated by administration of the recombinant ADAMTS13 in both knockout mice and wild-type mice.

FIG. 13 left is quantification of platelet fluorescence immunostaining of FIG. 12 using image analysis software (Image-J, NIH, U.S.A.) and shows that a lot of platelet coagulation in knockout mice and wild-type mice is markedly ameliorated by administration of the recombinant ADAMTS13. FIG. 13 right is a graph showing the measurement of blood flow of the liver tissue (microcirculation) measured with Laser Doppler Flowmeter (02C, LEA, Germany). It is shown that the blood flow of the liver tissue (microcirculation) is ameliorated with inverse correlation with the formation of platelet thrombi in the liver tissue.

FIG. 14 is a graph showing the transaminase release (A and B) and the LDH release (C) after IRI. It was shown that liver damage was aggravated in ADAMTS13 knockout mice as compared to wild-type mice but the liver damage was markedly ameliorated by administration of the recombinant ADAMTS13 in both knockout mice and wild-type mice.

FIG. 15 is a photograph showing a liver tissue image after hepatic ischemia and reperfusion. It is shown that the tissue damage in both knockout mice and wild-type mice is ameliorated by the recombinant ADAMTS13.

FIG. 16 is a graph showing that the tissue damage in both knockout mice and wild-type mice is ameliorated by the recombinant ADAMTS13.

FIG. 17 is a graph showing that ADAMTS13 suppresses the expression of inflammatory cytokines (TNFα, IL-1β, IL-6, IL-10) and chemokines (CXCL-2, -10) after IRI.

FIG. 18 is a photograph and a graph immunohistologically showing that infiltration of macrophages (monocytes) in knockout mice and wild-type mice is ameliorated by the recombinant ADAMTS13.

FIG. 19 is a photograph and a graph immunohistologically showing that infiltration of neutrophils in knockout mice and wild-type mice is ameliorated by the recombinant ADAMTS13.

FIG. 20 is a photograph and a graph immunohistologically showing that cell death by apoptosis in knockout mice and wild-type mice decreases by the recombinant ADAMTS13.

FIG. 21 is a photograph during surgery of a rat model of 20% partial liver transplantation.

FIG. 22 is a graph showing the ADAMTS13 activity after administration of the recombinant ADAMTS13 (W688X) to a model of 20% partial liver transplantation.

FIG. 23 is a graph showing the LDH release (A) and thrombocytopenia (B) after 20% partial liver transplantation. Both are ameliorated in the group of ADAMTS13 administration.

FIG. 24 is a photograph and a graph showing the CD42B fluorescence immunostaining after 20% partial liver transplantation (the platelets in the liver tissue are densely red-stained with fluorescence). It is shown that the platelet coagulation in the transplanted liver markedly decreases by administration of the recombinant ADAMTS13 to a model of 20% partial liver transplantation.

FIG. 25 is a graph showing the transaminase release after 20% partial liver transplantation. It is shown that liver damage is significantly suppressed by administration of the recombinant ADAMTS13.

FIG. 26 is a photograph and a graph showing that normality of the transplanted liver was maintained by administration of the recombinant ADAMTS13 to a model of 20% partial liver transplantation from the pathological point of view.

FIG. 27 is a photograph and a graph showing the histological immunostaining of vWF, which causes platelet coagulation, in the transplanted liver. It is shown that vWF, which originally is not expressed, is excessively expressed in the sinusoid in the liver tissue after transplantation and that the expression of vWF, which acts as a core of platelet coagulation, markedly decreased by administration of the recombinant ADAMTS13 to a model of 20% partial liver transplantation.

FIG. 28 is a photograph and a graph showing the cytokines (IL-1β, IL-6, TNFα) and the vasoconstrictor (Endothelin-1) markedly decreased by administration of the recombinant ADAMTS13 to a model of 20% partial liver transplantation.

BEST MODE FOR CARRYING OUT THE INVENTION

Figure 1:
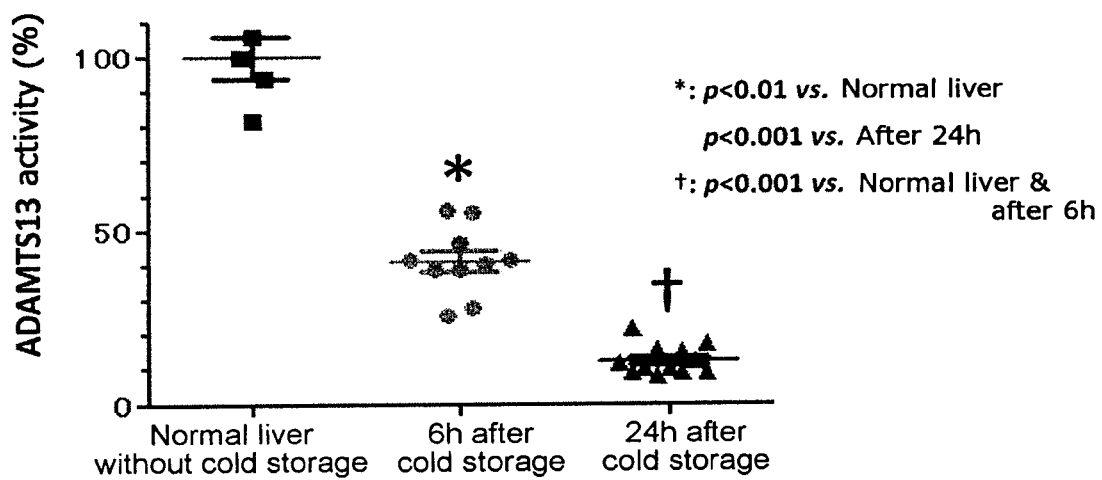
FIG. 1 shows cold storage/warm reperfusion injury in liver transplantation. There was no significant difference of a hepatic deviation enzyme (i.e. hepatocyte damage) after resumption of blood flow between two groups of cold storage for 6 and 24 hours. However, the ADAMTS13 activity was very accurately inversely correlated with the duration of cold storage of liver graft. This proves that the cold ischemic reperfusion is more harmful to the sinusoidal wall than to hepatocytes.

<Role of ADAMTS13 in Acute and Chronic Liver Damage: As Marker of Function of Liver Non-Parenchymal Cells in Various Liver Diseases and Possibility of Gene Recombinant ADAMTS13 for Therapeutic Application>

As described above, the present inventors focused on the hepatic non-parenchymal cells which have not been heretofore considered and evaluated the function thereof. ADAMTS13 is produced and secreted by the hepatic non-parenchymal cells, the stellate cells. Therefore, when the liver damage is severe, the ADAMTS13 activity in blood markedly decreases not to allow for cleavage of vWF-Multimers, which act as a core of platelet coagulation, to thereby induce thrombotic microangiopathy (TMA).

Furthermore, it was also found that the function of liver non-parenchymal cells markedly decreases by cold storage of the transplanted liver. The present inventors have found that there was no significant difference of a hepatic deviation enzyme (i.e. no significant difference of hepatocyte damage) between two groups of cold storage of the transplanted liver for 6 and 24 hours but that the ADAMTS13 activity was very accurately inversely correlated with the duration of cold storage of the transplanted liver, suggesting that ADAMTS13 can be an index indicating integrity of the sinusoidal cells constituting the sinusoidal wall of the liver.

Furthermore, the present inventors have found that the essence of liver damage after chemotherapy of colorectal cancer is a disorder of hepatic non-parenchymal cells. Namely, it was found that the essence of liver damage after chemotherapy of colorectal cancer (so-called "Blue Liver") is congestive liver due to destruction of the sinusoidal cells. In its animal model, SOS (Sinusoidal Obstructive Syndrome), the ADAMTS13 activity in the liver tissue and in blood was found to be an index very accurately indicating integrity of the sinusoidal cells constituting the sinusoidal wall of the liver. No difference of AST/ALT was observed between the groups.

Furthermore, the present inventors have found that the ADAMTS13 activity in blood is inversely correlated with the degree of liver failure (clinical data), suggesting that ADAMTS13 can be an index for the function of the hepatic non-parenchymal cells/sinusoid also in chronic liver diseases.

Further, the present inventors investigated the ADAMTS13 activity at an early stage after living donor liver transplantation to find that the activity markedly decreased at an early stage after liver transplantation in all the cases, that in comparison of the ADAMTS13 activity after liver transplantation between adult and infant, recovery of the ADAMTS13 activity was quicker in transplantation from adult to infant (liver graft of 1-5% weight ratio) than in transplantation from adult to adult (liver graft 0.6-1.5% weight ratio), and that in the case of adult the recovery of the ADAMTS13 activity was further delayed in relative insufficient graft, suggesting that the ADAMTS13 can be an index for the function of the hepatic non-parenchymal cells/sinusoid after liver transplantation. Besides, both the marked increase of the vWF activity and the marked decrease of the ADAMTS13 activity occur at an early stage after liver transplantation and thus there is imbalance of vWF/ADAMTS13 ratio and severe liver damage is potentially in the state of pre-TMA. After liver transplantation, though the degree may vary, almost all the cases are in the state of pre-TMA. Organ dysfunction after organ transplantation (Delayed Graft Function; DGF) is induced by microcirculation disturbance together with the formation of platelet thrombi in the transplanted liver/platelet decrease in peripheral blood. This is a lethal condition for partial liver transplantation in which the hepatic spare ability is insufficient.

From the above, it was found that the decrease in the ADAMTS13 activity was observed for all the acute and chronic conditions including cirrhosis, the perioperative period for liver transplantation, SOS and cold storage of the transplanted liver and these were found to correlate with the function of the sinusoidal cells. In case of the conditions where the accelerated vWF activity is observed, for instance, acute liver failure such as the perioperative period for liver transplantation and fulminant hepatitis, TMA is developed from the formation of the platelet thrombus in the blood vessel from vWF/ADAMTS13 imbalance and this is fatal. Therefore, it was suggested that ADAMTS13 is not only useful as a marker of "the function of the hepatic non-parenchymal cells", which has not been heretofore considered, but also is very promising as a therapeutic agent in severe liver damage.

<Role of ADAMTS13 in Hepatic Ischemia/Reperfusion Injury: Investigation Using Knockout Mice and Wild Type Mice and Protective Effect of Gene Recombinant ADAMTS13>

Using ADAMT13 knockout mice and wild type mice, the present inventors investigated in hepatic ischemia/reperfusion injury model whether or not ischemia/reperfusion injury is exacerbated in ADAMT13 knockout mice and whether or not the exacerbation is eliminated by administration of the recombinant ADAMTS13 to find that hepatic ischemia/reperfusion injury is markedly exacerbated in ADAMT13 knockout mice and that the exacerbation is completely eliminated by administration of the recombinant ADAMTS13, suggesting that ADAMTS13 has a significant protective effect on hepatic ischemia/reperfusion injury. It was also found that ADAMTS13 inhibited inflammatory cytokine expression after IRI.

Next, the present inventors investigated whether or not the recombinant ADAMT13 may exert protective effect on wild type mice like ADAMT13 deficient mice. As a result, also in wild type mice (=normal adult), both the marked increase of the vWF activity and the marked decrease of the ADAMTS13 activity occurred by hepatic ischemia/reperfusion injury, vWF/ADAMTS13 imbalance was significant and hepatic ischemia/reperfusion injury was significantly decreased by ADAMTS13, suggesting that ADAMTS13 can be used as a therapeutic agent for various hepatic diseases in normal adult having no genetic mutation.

<Role of ADAMTS13 in Liver Transplantation: Investigation Using 20% Partial Liver Transplantation Model and Protective Effect of Gene Recombinant ADAMTS13>

As described above, vWF/ADAMTS13 imbalance is observed in all the case after liver transplantation to a greater or lesser extent and is extreme in the case of early death since the ADAMTS13 activity produced by the stellate cells markedly decreases by cold storage inevitable for liver transplantation and, the smaller a size of transplanted liver is, the lower the ADAMTS13 activity becomes at an early stage after surgery. Viewing this, using rat partial liver transplantation model, the present inventors investigated protective effect when the recombinant ADAMTS13 is administered after adult living donor liver transplantation. The survival rate after 20% partial liver transplantation was examined. The survival rate on the fourth day was 100% and excellent in specimen sampling, at the same time the seven-day survival was 60%, and the effect of the therapeutic effect on survival could be evaluated as a main end point. As a result, it was found that transaminase release was suppressed by administration of the recombinant ADAMTS13 and the hepatocyte damage after 20% partial liver transplantation was significantly reduced. It was also found that, by administration of the recombinant ADAMTS13, LDH release was suppressed, and thrombotic microangiopathy (TMA conditions) significantly decreased. From the pathological point of view, the normality of the transplanted liver was maintained by administration of the recombinant ADAMTS13 to a model of 20% partial liver transplantation. From this, it was suggested that the recombinant ADAMTS13 had a protective effect on the transplanted liver even in a rat model of 20% partial liver transplantation mimicking living donor liver transplantation (adult) and was promising as a new therapeutic agent.

<Protective Effect of ADAMTS13 in Acute Liver Failure/Fulminant Hepatitis: Study in Rat Acute Liver Failure Model Using Thioacetamide (TAA)>

The mortality rate of fulminant hepatitis is still high in recent years and the life-saving rate is as low as 40% in conservative (medical) treatment and is 80% even in the case of liver transplantation. The present inventors have found that the survival rate became drastically high when the recombinant ADAMTS13 was administered in a rat acute liver failure model using Thioacetamide (TAA).

<ADAMTS13 and its Mutants>

ADAMTS13 as used herein is metalloprotease of ADAMTS13 (a disintegrin-like and metalloproteinase with thrombospondin type 1 motifs 13) family which cleaves vWF between the residues Tyr1605 and Met1606. In the context of the present invention, ADAMTS13 includes the one from, for example, a mammal, e.g. primate, human (NP_620594), monkey, rabbit, pig, bovine (XP_610784), rodents, mouse (NP_001001322), rat (XP_342396), hamster, sand rat, dog, cat, frog (NP_001083331), chicken (XP_415435) and the like, and biologically active derivatives thereof. ADAMTS13 as used herein also includes mutants with the activity and mutant ADAMT13 proteins as well as functional fragments of ADAMTS13 proteins and fusion proteins. Additionally, the ADAMT13 proteins of the present invention may further include tags that facilitate purification, detection or both of them. The ADAMTS13 protein described herein may be further modified by a treatment part or a part suitable for in vitro or in vivo imaging.

The term "biologically active derivative" as used herein refers to any polypeptide having substantially the same biological function as ADAMTS13. A polypeptide sequence of a biologically active derivative may include deletion, addition and/or substitution of one or more amino acids, whose absence, presence and/or substitution has no substantial negative effect on the biological activity of the polypeptide. The biological activity of the polypeptide may be measured by, for example, the reduction or delay of platelet adhesion to the endothelium, the reduction or delay of platelet aggregation, the reduction or delay of the formation of platelet strings, the reduction or delay of thrombus formation, the reduction or delay of thrombus growth, the reduction or delay of the occlusion of the blood vessel, the proteolytic cleavage of vWF, and the collapse of thrombus, or by the cleavage of peptide substrates such as, for example, FRETS-VWF73 peptide (Kokame et al., Br J Haematol. 2005 April; 129(1): 93-100) or a mutant thereof.

For ADAMTS13 as used herein, both ADAMTS13 derived from blood (hereinafter also referred to as "nADAMTS13") and a recombinant ADAMTS13 (hereinafter also referred to as "rADAMTS13") obtained by the gene recombination technique can be used. ADAMTS13 as used herein may also be a mutant in which a mutation is introduced into a part of the amino acids of ADAMTS13 or a minimum unit having the cleavage activity (hereinafter also referred to as "mADAMTS13") as far as they have the enzymatic activity to cleave vWF. Therefore, ADAMTS13 referred to in the present invention also includes nADAMTS13, rADAMTS13 and mADAMTS13.

Human ADAMTS13 includes, but is not limited to, a polypeptide comprising the amino acid sequence of Gen-Bank accession number NP_620594 or its processed product, for example, a polypeptide in which a signal peptide (amino acid residues (1-29) and/or a propeptide (amino acid residues 30-74) are removed. Many natural mutants of human ADAMTS13 are known in the art and are encompassed by the formulation of the present invention, a part of which includes mutations selected from R7W, V88M, H96D, R102C, R193W, T196I, H234Q, A250V, R268P, W390C, R398H, Q448E, Q456H, P457L, P475S, C508Y, R528G, P618A, R625H, I673F, R692C, A732V, E740K, A900V, S903L, C908Y, C951G, G982R, C1024G, A1033T, R1095W, R1095W, R1123C, C1213Y, T12261, G1239V and R1336W. ADAMTS13 further includes natural and recombinant proteins mutated, for example, by one or more conservative mutations in non-essential amino acids. It is preferable that the amino acids essential for the enzymatic activity of ADAMTS13 is not mutated. These amino acids include, for example, a residue which is known or estimated to be essential for metal bonding, for example, the residues at positions 83, 173, 224, 228, 234, 281 and 284, and residues found in the active site of the enzyme, for example, the residue at position 225. Similarly, in the context of the present invention, ADAMTS13 also includes an isoform, for example, an isoform that lacks the amino acid residues at positions 275-305 and/or 1135-1190 of the full-length human protein.

These mutations may be the one generated spontaneously or the one generated by artificial mutagenesis. Artificial mutagenesis is well known in the art and includes, for example, site-specific mutagenesis using recombinant method, synthesis of mutant polypeptides by chemical methods such as, for example, solid phase synthesis and liquid phase synthesis, or chemical modification of amino acid residues, details of which are well known to those skilled in the art. Such mutation and/or modification may be at any position.

In order to introduce a point mutation to the resulting ADAMTS-13 gene, site-directed mutagenesis may generally be used. Practically, the introduction of a point mutation to the ADAMTS-13W688X gene is conducted using a commercially available kit such as Site-Directed Mutagenesis System (Takara: Mutan-Super Express Km, Mutan-Express Km, Mutan-K, and the like), QuickChange Multi Site-Directed Mutagenesis Kit, QuickChange XL Site-Directed Mutagenesis Kit (Stratagene) and GeneTailor Site-Directed Mutagenesis System (Invitrogen) applying said technique in accordance with the appended protocol.

In particular, when ADAMTS13 of the present invention is produced in an expression system of eukaryotic cells, there is a high possibility that sugar chains are added to serine or threonine residues in the polypeptide. Thus, ADAMTS13 which is expressed in eukaryotic cells and added with sugar chains is also included in the present invention.

By incorporating the ADAMTS13 gene or the mADAMTS13 gene with introduction of a point mutation into an appropriate expression vector and transforming a host with the expression vector, the expression of the recombinant ADAMTS13 (rADAMTS13 protein) and its mutants (mADAMTS13 protein) is performed. For a host, as commonly used for expression of a foreign protein, bacteria, yeast, animal cells, plant cells and insect cells can be used. However, any host may be used as far as substantially the same biological function as ADAMTS13 is maintained. When rADAMTS13 protein or mADAMTS13 protein are purified from cells producing these proteins, a purification method commonly used in protein chemistry is used. The above-mentioned modifications can also be carried out by a chemical method.

Similarly, ADAMTS13 may be further modified by, for example, post-translational modification (for example, glycosylation of one or more amino acid residues selected from human residues 142, 146, 552, 579, 614, 667, 707, 828, 1235, 1354, or naturally or artificially modified sites), or by chemical or enzymatic modification in ex vivo including, but not limited to, glycosylation, modification with water-soluble polymers (e.g., PEGylation, sialylation, modification with HES, etc.) and tagging.

Examples of modification of amino acids include acetylation, acylation, amidation, addition of a sugar chain, addition of a nucleotide or a nucleotide derivative, addition of a lipid or a lipid derivative, cyclization, formation of disulfide bond, demethylation, crosslinking, formation of cystine, formation of pyroglutamic acid, formylation, hydroxylation, halogenation, methylation, oxidation of a side chain, treatment with a proteinase, phosphorylation, sulfation, racemization, etc., which are well known in the art.

Particularly preferable in the present invention as ADAMTS13 mutant is a molecule containing a minimum unit of ADAMTS13 exerting the activity, i.e. from a metalloprotease domain to a spacer domain of ADAMTS13, in particular, C-terminal deletion mutant W688X (cf. WO 2004/029242 pamphlet; Soejima, K. et al.: ADAMTS-13 cysteine-rich/spacer domains are functionally essential for von Willebrand factor cleavage. Blood, 102: p. 3232-3237, 2003; hereinafter also referred to as "ADAMTS-13W688X protein") provided by deleting the amino acid residues ranging from the 689th amino acid to the C terminus from the 1427 amino acid residues of ADAMTS13. The gene W688X encoding the minimum unit of ADAMTS13 exerting the activity (hereinafter also referred to as "ADAMTS13 gene") may be obtained, for example, by designing a PCR primer on the basis of the sequence as described in Non-patent reference 7 and Patent reference 3 and conducting PCR using as a template cDNA derived from human organs or cells producing ADAMTS13. In particular, the ADAMTS13 gene may be prepared as described below. First, total RNAs are extracted from human hepatocytes and then mRNAs are purified therefrom. The resulting mRNAs are converted to cDNAs, then PCR reaction is conducted using PCR primers designed depending on each of the gene sequences, and the resulting PCR products are incorporated into a plasmid vector which is introduced into E. coli. The clone containing cDNA encoding the desired protein is chosen among E. coli colonies. For the extraction of total RNAs, commercially available reagents such as TRIzol reagent (GIBCO BRL) and ISOGEN (NIPPON GENE Co., Ltd.) may be used. For the purification of mRNAs, commercially available kits such as mRNA Purification Kit (Amersham BioSciences) may be used. For the conversion to cDNAs, commercially available kits for preparing cDNA library such as SuperScript plasmid system for cDNA synthesis and plasmid cloning (GIBCO BRL) may be used. For practically obtaining the ADAMTS13 gene, a commercially available cDNA library such as e.g. Human Liver Marathon-Ready cDNA (BC Bioscience) may be used. The PCR primers are readily available from companies in charge of DNA synthesis (e.g. QIAGEN). It is preferred that KOZAK sequence (Kozak M, J. Mol. Biol., 196, 947 (1987)) and an adequate sequence of a restriction enzyme cleavage site is added to the 5' side of the primer. The PCR reaction may be conducted using a commercially available Advantage HF-2 PCR Kit (BC Bioscience) in accordance with the appended protocol. The base sequence of DNA fragments obtained from PCR is determined by a DNA sequencer, e.g. CEQ2000XL DNA Analysis System (Beckman) after the cloning using a TA cloning kit (Invitrogen Corporation) etc.

To purify the ADAMTS13 protein or the ADAMTS13 mutant from the cells producing said protein, a purification method generally used in the protein chemistry may be used. The purification method includes, for example, centrifugation, salting-out, ultrafiltration, isoelectric precipitation, electrophoresis, ion-exchange chromatography, gel filtration, affinity chromatography, hydrophobic chromatography, hydroxyapatite chromatography and CS resin chromatography in combination thereof. An amount of the obtained protein may be measured using a reagent for protein measurement such as BCA Protein Assay Reagent Kit (Pierce Biotechnology, Inc), Protein Assay Kit (BIO-RAD, Inc), and the like.

The detection of the ADAMTS13 protein may be conducted by a method on the basis of a molecular size such as SDS-PAGE, gel filtration, and the like or a method on the basis of an antigen-antibody reaction such as ELISA, Western blot, dot blot, and the like. The above methods are all commonly used to determine a foreign protein and may be selected in accordance with the purpose. An amount of the obtained ADAMTS13 protein may be measured using a reagent for protein measurement such as BCA Protein Assay Reagent Kit (Pierce Biotechnology, Inc), Protein Assay Kit (BIO-RAD, Inc), and the like.

The enzymatic activity of ADAMTS13 may be measured by, for example, a method using SDS agarose electrophoresis (M. Furlan et al., Blood, US, 1997, Vol. 89, p. 3097-3103), ELISA using a recombinant antigen of the A2 domain of the substrate vWF (Whitelock J L et al., Journal of thrombosis and hemostheres, UK, 2004, Vol. 2, 485-491), or a method using the quencher fluorescent substrate FRETS-VWF73, which is a synthetic peptide corresponding to 73 residues of Asp1596-Arg1668 in the A2 domain of vWF in which a fluorescent group [2-(N-methylamino)benzoyl, Nma] and an extinction group (2,4-dinitrophenyl, Dnp) are introduced (Kokame K et al., British Journal of Hematology, U K, 2005, Vol. 129, 93-100). The enzymatic activity of ADAMTS13 may be measured by a method described in Japanese patent application No. 2005-148793, specifically, an analytical method comprising (1) a step of contacting a sample to be tested which is suspected to contain ADAMTS13 and an immobilized substrate which is an insoluble carrier to which vWF or a fragment thereof is bound in a solution, (2) a step of separating the solution and the insoluble carrier, and (3) a step of analyzing vWF or a fragment thereof remaining on the insoluble carrier and/or vWF or a fragment thereof which is released from the insoluble carrier and is present in the solution.

To evaluate the activity of the ADAMTS13 protein, the activity to bind to or degrade vWF derived from human plasma or partially synthesized peptide of vWF may be measured by a method such as ELISA and the like using an antibody to ADAMTS13 or an antibody to a tag when an antibody with tagging is used. ELISA may be constructed by a common procedure. vWF derived from human plasma and an antibody to ADAMTS13 for ELISA may be obtained according to the methods of Soejima, K. et al. (J. Biochem., 130: p. 475-480, 2001) and Soejima, K. et al. (J. Biochem., 139: p. 147-154, 2006). A commercially available fluorescently-labeled FRETS-VWF73 (PEPTIDE INSTITUTE, INC.) may be used as a partially synthesized peptide of vWF.

<ADAMTS13 Composition and Formulation>

ADAMTS13 or its mutant of the present invention may be formulated into a pharmaceutical preparation for treatment, diagnosis or other uses. For example, to prepare a preparation for intravenous administration, a composition may generally be dissolved in an aqueous solution that contains physiologically compatible materials such as sodium chloride, glycine etc. and has a physiologically compatible, buffered pH. A lyophilized formulation may be employed as a final form to enable prolonged stability. A guideline for a composition for intravenous administration is established by the Government's regulation, e.g. "Minimum Requirements for Biological Products". A pharmaceutical composition of the present invention comprising as an active ingredient ADAMTS13 or its mutant may specifically be used in patients having a reduced ADAMTS13 level such as patients with liver damage, hepatic ischemia/reperfusion injury, the liver function after liver transplantation and/or acute liver failure/fulminant hepatitis. Alternatively, said pharmaceutical composition may be used as a supplemental treatment in patients with an elevated blood concentration of vWF, a substrate of this enzyme, or in patients foreseen to develop ULVWF due to inflammation etc.

The pharmaceutical composition of the present invention, in addition to ADAMTS13 or its mutant, may further comprise a pharmaceutically acceptable additive commonly used in a pharmaceutical preparation (for example, a carrier, an excipient, a diluent, and the like), a stabilizing agent or a pharmaceutically necessary ingredient. The stabilizing agent includes monosaccharides such as glucose, disaccharides such as saccharose and maltose, sugar alcohols such as mannitol and sorbitol, neutral salts such as sodium chloride, amino acids such as glycine, polyethylene glycol, polyoxyethylene-polyoxypropylene copolymer (pluronic), non-ionic surfactants such as polyoxyethylene sorbitan fatty acid ester (Tween), human albumin, and the like. The pharmaceutical composition of the present invention further includes other agents, an auxiliary agent, a tissue permeation promoter, a solubilizing agent, and the like. Such materials are non-toxic and do not interfere with the efficacy of the active ingredient. The exact nature of the carrier or other material may depend on a route of administration, for example, oral, intravenous, cutaneous or subcutaneous, nasal, intramuscular, or intraperitoneal administration. The carrier or other material may appropriately be selected depending on the route of administration. Methods for preparing a pharmaceutical composition and a formulation are known to those skilled in the art.

The pharmaceutical composition comprising ADAMTS13 or its mutant of the present invention may be formulated e.g. for intravenous administration (e.g. as a bolus, or by sustained injection over a long period of time), via intramuscular, intraperitoneal, intracerebral and intramedullary, subcutaneous, intra-articular, intrasynovial, intraspinal, oral, topical or inhalational route of administration. In certain embodiments, the ADAMTS13 formulation of the present invention can be administered systemically or topically. Systemic administration includes, but is not limited to, oral, subdermal, intraperitoneal, subcutaneous, nasal, sublingual or rectal administration. Topical administration includes, but is not limited to, topical, subcutaneous, intramuscular and intraperitoneal administration.

The pharmaceutical composition for oral administration may be tablets, capsules, powders, or liquids. The tablets may include solid carriers such as gelatin or adjuvants. The pharmaceutical composition in liquid is typically comprised of a liquid carrier such as water, petroleum, animal oils, vegetable oils, mineral oils, or synthetic oils, including saline, a solution of glucose or other saccharide or glycols such as ethylene glycol, propylene glycol, or polyethylene glycol.

In the case of intravenous, cutaneous or subcutaneous injection or injection into a pain site, an active ingredient does not include a pyrogen, and an aqueous solution that has suitable pH, isotonicity and stability and can be received extraintestinally is preferable. Those skilled in the art can prepare a suitable solution using, for example, isotonic media such as a sodium chloride solution, Ringer's solution, or lactated Ringer's solution. The solution may comprise a preservative, a stabilizing agent, a buffer, an antioxidant and/or other additives as needed.

The pharmaceutical compositions of the present invention can be administered in an effective amount by intravenous injection, intramuscular injection, subcutaneous injection or the like and is administered once or several times. The dose varies depending on symptoms, age, body weight, etc. and is 100 to 700 units/kg body weight, preferably 300 to 700 units/kg, more preferably 400 to 700 units/kg, per administration. A plurality of repeated administration or sustained administration is more preferable for the maintenance of the blood activity value.

<ADAMTS13 as Biomarker>

According to the present invention, the use of ADAMTS13 as a biomarker for monitoring the onset of liver damage, hepatic ischemia/reperfusion injury or the liver function after liver transplantation is provided. Furthermore, according to the present invention, a method of testing liver damage, a method of testing hepatic ischemia/reperfusion injury or a method of testing the liver function after liver transplantation, each of the methods comprising measuring or monitoring the ADAMTS13 activity in a sample of hepatic non-parenchymal cells from a mammal, is provided.

Such a method of testing is performed using a biological sample from a patient. These samples can be used directly without pretreatment, or a treatment such as removal of substances in a sample that can interfere by centrifugation or filtration may be performed before performing the assay. As the test sample, for example, blood in the form of plasma or serum is preferable but various bodily fluids such as, for example, cell tissue liquid, lymph, thymus fluid, ascites, amniotic fluid, gastric fluid, urine, pancreatic fluid, bone marrow fluid or saliva can also be used. The plasma is preferably citrated plasma or heparin plasma.

In accordance with the method of testing of the present invention, the ADAMTS13 activity in a biological sample of a patient is measured and, when the activity is lower than a given activity, liver damage, hepatic ischemia/reperfusion injury or hepatic dysfunction after liver transplantation is determined wherein the ADAMTS13 activity is generally evaluated as follows: up to 10%: possibility of severe blood disease or hepatic disease, urgent necessity of work-up; 11-30%: possibility of severe blood disease or hepatic disease, necessity of work-up; 31-80%: necessity of detailed examination; 81% or more: normal. In case of liver damage, evaluation is as follows: up to 10%: severe liver failure; 11-30%: severe hepatic dysfunction; 31-50%: necessity of detailed examination; 51-80%: detailed examination is preferable; 81% or more: normal. Furthermore, after liver transplantation, evaluation is as follows: up to 10%: liver dysfunction after transplantation, necessity of therapeutic intervention; 11-30%: hepatic dysfunction after transplantation, necessity of therapeutic intervention or a main treatment intervention or strict follow-up; 31-50%: strict follow-up; 51-80% (depending on post-operative days): follow-up; 81% or more (depending on the post-operative days): satisfactory progress.

In accordance with the method of the present invention, a method for analyzing the ADAMTS13 activity is not particularly limited as far as it can quantitatively or semi-quantitatively determine the activity of the ADAMTS13 and includes, for example, an immunological approach using an anti-ADAMTS13 antibody or a fragment thereof (for example, enzyme immunoassay, latex aggregation immunoassay, chemoluminescence immunoassay, fluorescent antibody method, radioimmunoassay, immunoprecipitation, immunohistochemical staining, Western blot, and the like), biochemical approach (for example, enzymatic measurement) or a molecular biological approach measuring the amount of mRNA, and the like. When immunological approach is used for analysis of the ADAMTS13, an anti-ADAMTS13 antibody may be prepared in accordance with a known method, for example, the method described in WO 2004/029242 pamphlet, and the immunological measurement may be carried out, for example, according to the method described in WO 2004/029242 pamphlet.

As a method for measuring the ADAMTS13 activity, an immunological method is preferable in view of sensitivity and simplicity. An immunological method includes various methods, for example, a competitive method with a labeled ADAMTS13, a sandwich method with a labeled antibody, a latex bead method in which aggregation of beads coated with an antibody is observed, or a method using an antibody bound to colored particles such as gold colloid. However, the method using the antibody to ADAMTS13 is included in a preferred embodiment of the present invention. The antibody may be a monoclonal antibody or a polyclonal antibody. An antibody fragment such as Fab, Fab', F(ab')$_2$ or Fv can also be used.

In accordance with the method of the present invention, in addition to the ADAMTS13 activity in a sample, the vWF concentration may also be measured and from the ratio of both of them, liver damage, hepatic ischemia/reperfusion injury or hepatic dysfunction after liver transplantation can be monitored. In case of thrombotic microangiopathy (TMA), imbalance of vWF/ADAMTS13 ratio (the vWF activity markedly increases whereas the ADAMTS13 activity markedly decreases) occurs. Therefore, by measuring both activity of vWF and ADAMTS13 and examining the ratio of the measured values, the above-mentioned diseases can be monitored. In this regard, a threshold for determination for various determinations, for example, a threshold for determination of the concentration of ADAMTS13 and the ADAMTS13 activity, and a threshold for determination of the ratio of the concentration of ADAMTS13 or the activity thereof to vWF is preferably determined in advance.

A method for measuring the concentration of vWF includes, for example, an activity measurement method by the aggregation activity of human platelets and ristocetin cofactor (Allain J P et al., J Lab Clin Med. UAS, 1975, Vol. 85, p. 318-328) or an immunoassay using an anti-vWF antibody (Brown J E et al., Thromb Res. USA, 1986, Vol. 43, p. 303-311), and the like. An immunological method is preferable from the viewpoint of sensitivity and simplicity.

<Kit>

The present invention also provides a kit for monitoring the onset of liver damage, a kit for monitoring hepatic ischemia/reperfusion injury, and a kit for monitoring the liver function after liver transplantation, each of the kit comprising a means for measuring the ADAMTS13 activity in a sample from a mammal.

In accordance with the kit of the present invention, the means for measuring the ADAMTS13 activity in a sample may be, for example, an anti-ADAMTS13 antibody or a fragment thereof. Two or more different anti-ADAMT13 antibodies are preferably included. The anti-ADAMTS13 antibody may be either a monoclonal antibody or a polyclonal antibody. In case that two or more different anti-ADAMT13 antibodies are included, either (second antibody) of the two can be used as a labeled antibody, or instead of labeling, a labeled antibody in which a label is bound to an antibody to the second antibody can be further added to the kit.

The invention also provides a method for measuring the ADAMTS13 activity in hepatic non-parenchymal cells taken from a mammal and to screen the reduction of ADAMTS13 activity. The reduction of the ADAMTS13 activity in hepatic non-parenchymal cells of a mammal can be an index of acquiring of the diseases selected from the group consisting of liver damage, hepatic ischemia/reperfusion injury and hepatic dysfunction after liver transplantation in a mammal.

In the following, the present invention is explained in more detail by means of examples. It should be noted that the present invention is not limited to the following examples.

Example 1

<Function of Hepatic Non-Parenchymal Cells Markedly Decreases by Cold Storage of Transplanted Liver>

After the entire liver was taken from rats (Wistar Rat, male, 250 to 270 g), the ADAMTS13 activity was measured in the liver tissue after simple cold storage in HTK solution for 6 hours and 24 hours and plotted with a relative ratio to 100% of the average activity value in four cases of rat normal liver without storage (FIG. 1). The ADAMTS13 activity was measured by FRET (FRETS-VWF73: PEPTIDE INSTITUTE, INC.).

As a result, there was no significant difference of a hepatic deviation enzyme (no significant difference of hepatocyte damage) between two groups of cold storage of the transplanted liver for 6 and 24 hours but the ADAMTS13 activity in the liver tissue was very accurately inversely correlated with the duration of cold storage of the transplanted liver (FIG. 1).

Example 2

<Essence of Liver Damage after Chemotherapy of Colorectal Cancer is Disorder of Hepatic Non-Parenchymal Cells>

Figure 2:
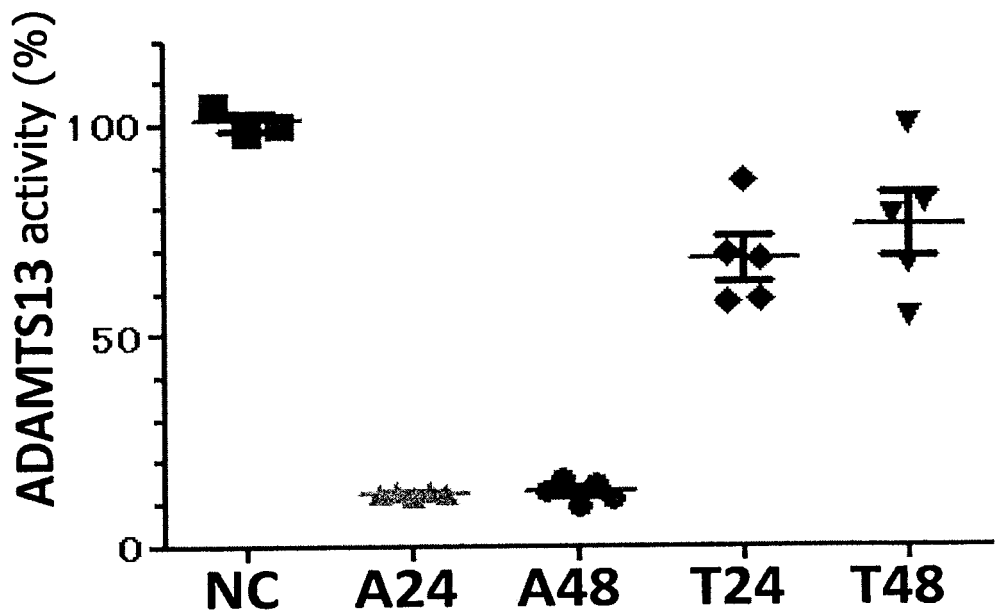
FIG. 2 is a graph showing that the essence of liver damage after chemotherapy of colorectal cancer is a disorder of hepatic non-parenchymal cells. Hepatocyte damage (AST/ALT, etc.) was slight and the function of hepatocytes such as protein synthesis ability and coagulation ability was within a normal range. However, the ADAMTS13 activity was reduced to as low as 12% of normal liver. This is a disorder of hepatic non-parenchymal cells which is hardly evaluated in modern medical treatment and is one of the main factors causing liver dysfunction after liver resection of metastatic liver tumor of colorectal cancer. NC: normal liver; A24: 24 hours after monocrotaline administration; A48: 48 hours after monocrotaline administration; T24: 24 hours after administration of monocrotaline plus the treating agent; T48: 48 hours after administration of monocrotaline plus the treating agent

Oxaliplatin, one of the key drugs of chemotherapy for colorectal cancer, causes liver damage at a high rate. The essence of the pathological condition is sinusoidal obstructive syndrome (SOS) caused by destruction of the sinusoidal cells by oxaliplatin. Using a monocrotaline administration model commonly used as an SOS animal model, the ADAMTS13 activity values after 24 and 48 hours of administration were compared with or without administration of the treating agent (in each group, n=5). As in FIG. 1, the liver tissue was taken and quantification was made by FRET.
NC: normal liver
A24: 24 hours after monocrotaline administration
A48: 48 hours after monocrotaline administration
T24: 24 hours after administration of monocrotaline plus the treating agent
T48: 48 hours after administration of monocrotaline plus the treating agent As a result, the ADAMTS13 activity, which markedly decreased before administration of the treating agent, markedly recovered after administration of the treating agent (FIG. 2). From this, it was found that the essence of liver damage after chemotherapy of colorectal cancer is congestive liver due to destruction of the sinusoidal cells and that the ADAMTS13 activity in the liver tissue and in blood was an index very accurately indicating integrity of the sinusoidal cells constituting the sinusoidal wall of the liver. No difference of an index of hepatocyte damage, AST/ALT, was observed between the groups.

Example 3

<ADAMTS13 Activity in Blood is Inversely Correlated with Degree of Liver Failure>

Figure 3:
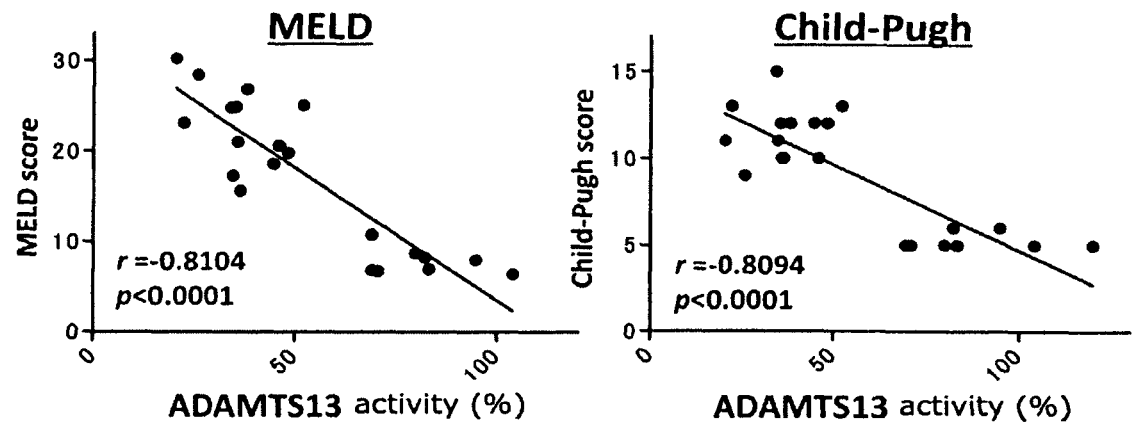
FIG. 3 is a graph showing the clinical data that the ADAMTS13 activity in blood is inversely correlated with the degree of liver failure (MELD: Model for End-stage Liver Disease, Child-Pugh: Child score)

A pre-operative ADAMTS13 activity value, a MELD (Model for End-stage Liver Disease) score, which is most widely used throughout the world as an index of liver failure, and a child-PUGH score were monitored in 21 cases of donors and recipients of adult living donor partial liver transplantation performed in Kyoto University Hospital, Division of Hepato-Pancreato-Biliary Surgery and Transplantation from November, 2012 to March 2013. As a result, the pre-operative ADAMTS13 activity value showed very clear inverse correlation with the MELD score and the Child-Pugh score (FIG. 3). Namely, the blood ADAMTS13 activity value is considered to be useful as an index of liver failure.

Example 4

<ADAMTS13 Activity at Early Stage after Living Donor Liver Transplantation>

A blood ADAMTS13 activity value was monitored in 95 cases of living donor partial liver transplantation performed in Kyoto University Hospital, Division of Hepato-Pancreato-Biliary Surgery and Transplantation on consecutive days before surgery of recipients up till two weeks after surgery from October, 2010 to March 2012. It is apparent that the blood ADAMTS13 activity value decreased at an early stage after liver transplantation in all the cases.

Figure 4:
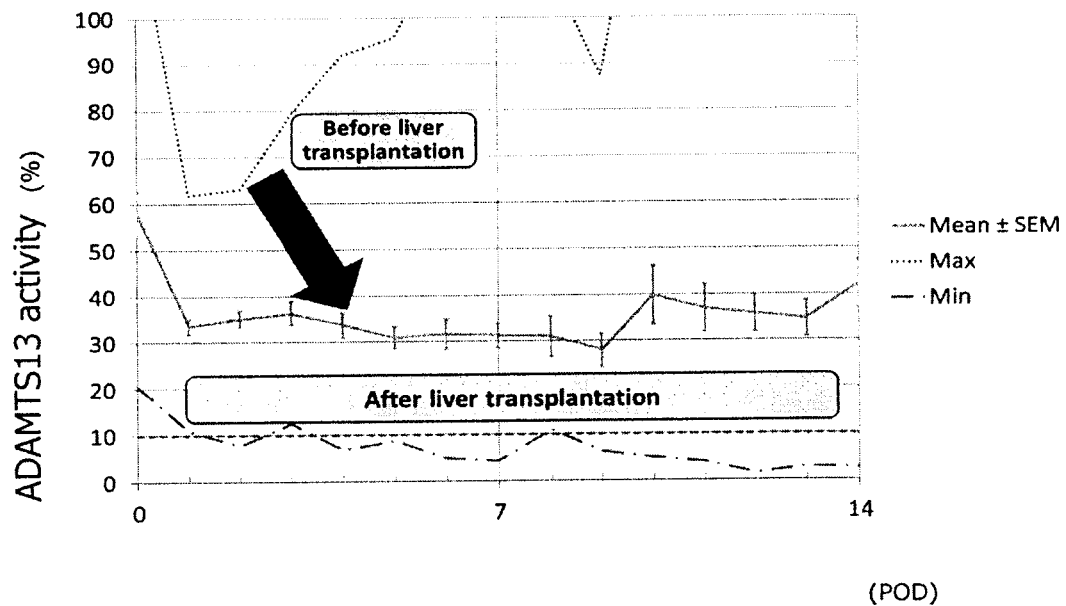
FIG. 4 is a graph showing that the ADAMTS13 activity decreases markedly at an early stage after living donor liver transplantation.

As a result, it was found that the ADAMTS13 activity decreased markedly at an early stage after living donor liver transplantation (FIG. 4). The results described above prove the effect of the cold storage of the transplanted liver on the non-parenchymal cells, the sinusoidal cells constituting the sinusoidal wall of the liver, through quantification of the proteins produced from the stellate cells, one of the non-parenchymal cells.

Example 5

<ADAMTS13 Activity after Liver Transplantation (Infant Vs Adult)>

95 cases of living donor partial liver transplantation performed in Kyoto University Hospital, Division of Hepato-Pancreato-Biliary Surgery and Transplantation from October, 2010 to March 2012 were divided into infant cases (n=29) and adult cases (n=66) and the ADAMTS13 activity value after liver transplantation was compared and studied.

Figure 5:
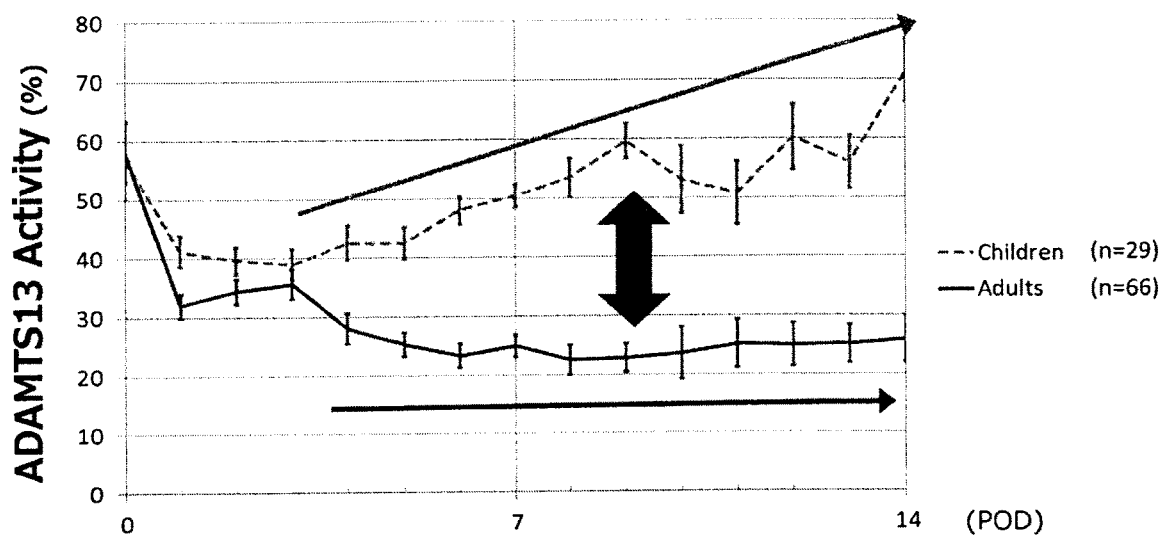
FIG. 5 is a graph showing the data that the ADAMTS13 activity after liver transplantation is compared between infant and adult.

The liver is the largest solid organ corresponding to about 2% (standard liver volume) of body weight. Transplantation from adult to infant is often carried out with liver graft of 1 to 5% weight ratio whereas transplantation from adult to adult is often carried out with liver graft 0.6 to 1.5% weight ratio. Recovery of the ADAMTS13 activity in the case of an infant was significantly good since the relative implanted liver capacity in the case of an infant was larger than that of an adult (FIG. 5).

Example 6

<Recovery of ADAMTS13 Activity is Further Delayed in Relative Insufficient Graft Even in the Case of Adult>

The adult 66 cases as described above were divided into two groups of 1.0% or more and less than 1.0% of a graft liver weight/recipient weight ratio (GRWR) and the ADAMTS13 activity value after liver transplantation was compared and studied. Recovery of the ADAMTS13 activity in the case of the group with less than 1.0% of GRWR (27 cases) tended to be delayed as compared to the group with 1.0% or more of GRWR (39 cases).

Figure 6:
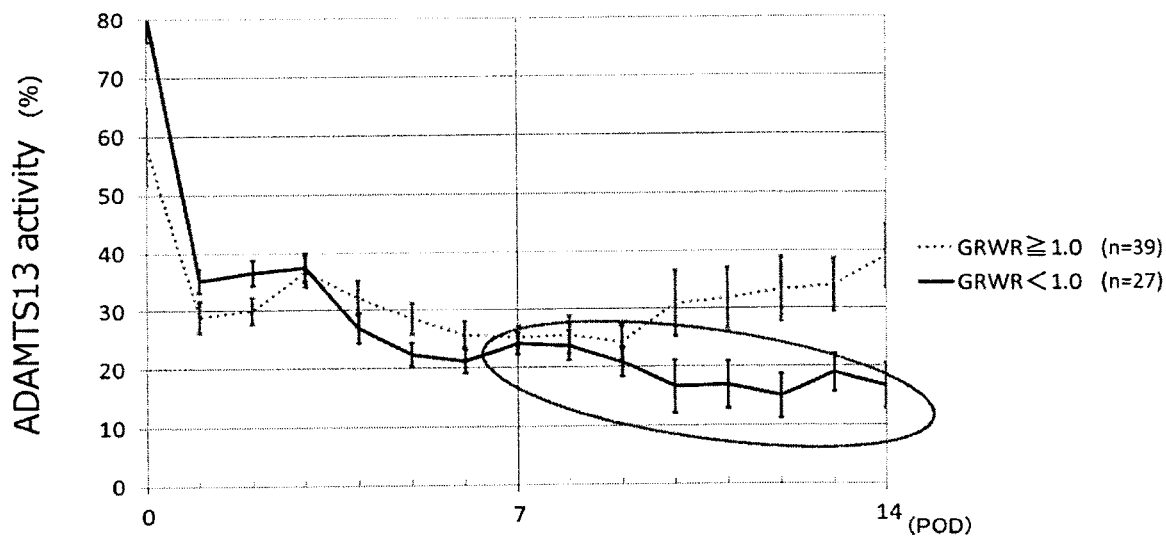
FIG. 6 is a graph showing that the recovery of the ADAMTS13 activity is further delayed in relative insufficient graft even in the case of adult.

From the above, it was found that the ADAMTS13 activity value in recipient blood after liver transplantation was well correlated with GRWR, the graft liver spare ability, suggesting that the ADAMTS13 can be an index for the function of the hepatic non-parenchymal cells/sinusoid after liver transplantation (FIG. 6).

Example 7

<Both Marked Increase of vWF Activity and Marked Decrease of ADAMTS13 Activity Occur at Early Stage after Liver Transplantation>

Figure 7:
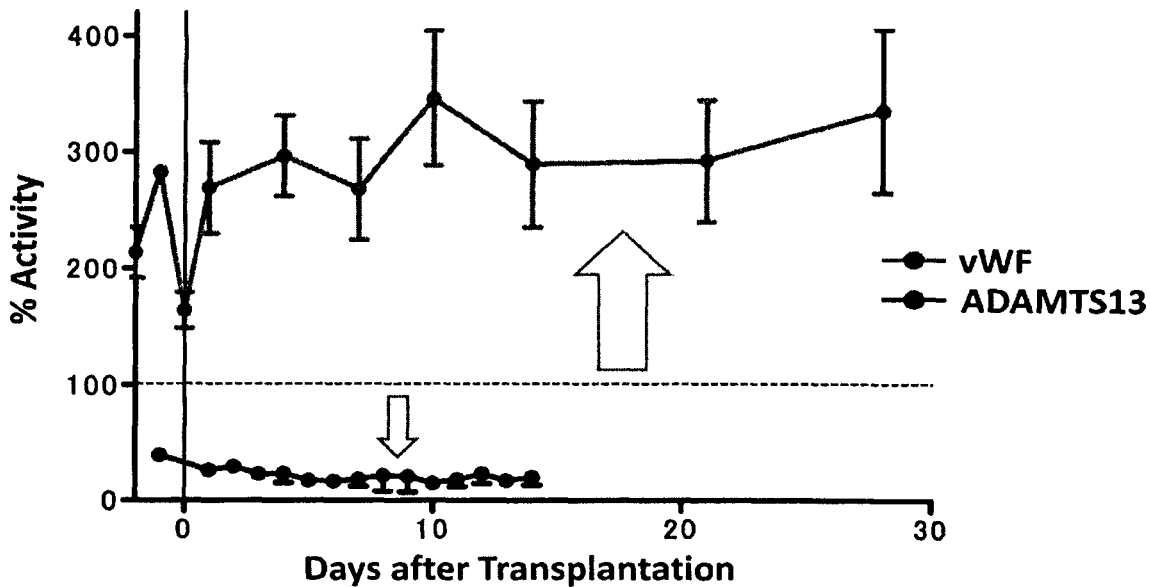
FIG. 7 is a graph showing that both the marked increase of the vWF activity and the marked decrease of the ADAMTS13 activity occur at an early stage after liver transplantation.

Both activity values of blood von Willebrand Factor (vWF; which becomes a nucleus of platelet thrombus, physiologically plays a role as a starting point of the hemostatic mechanism and is also a starting point of a pathological condition causing excessive aggregation of platelets in the vascular endothelial disorder or the like), and ADAMTS13, which is an enzyme cleaving platelet thrombus, were measured in 95 cases of adult living donor partial liver transplantation performed in Kyoto University Hospital, Division of Hepato-Pancreato-Biliary Surgery and Transplantation from July, 2013 to March 2015, and compared and studied (FIG. 7). Also, it was revealed that the relative ratio of vWF/ADAMTS13 (normal ratio is 1 when both of the activities in the normal human plasma are 100%) was 10 times or more higher in all patients after liver transplantation (FIG. 8, left) and 30 times or more higher in cases of early death (FIG. 8, right) in tendency of platelet thrombus formation.

Figure 8:
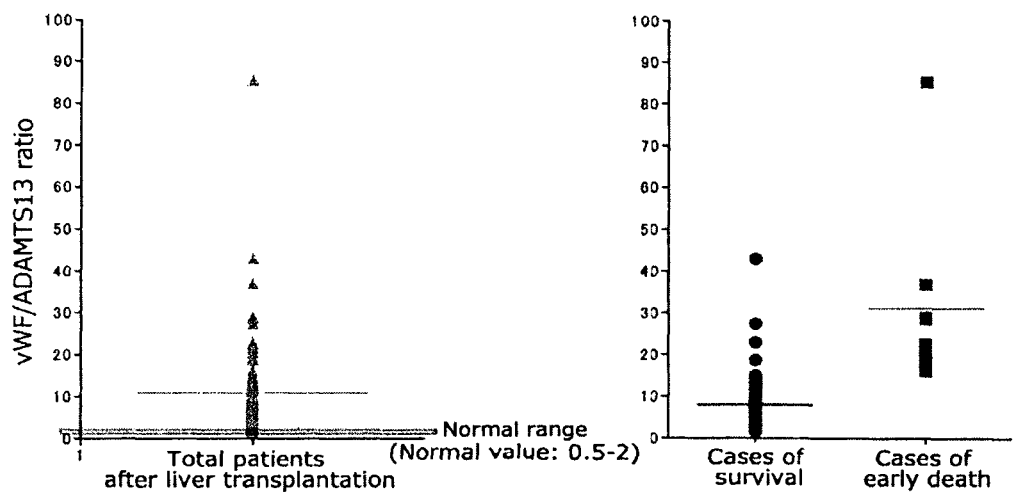
FIG. 8 is a graph showing that vWF/ADAMTS13 imbalance is observed after liver transplantation.
Figure 9:
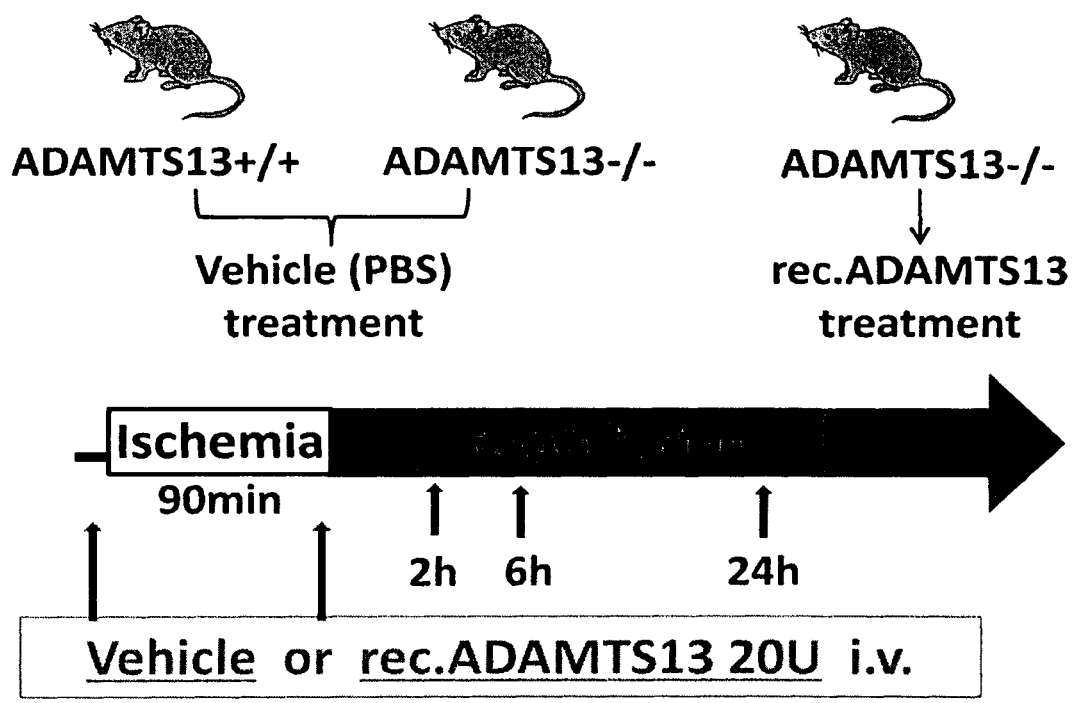
FIG. 9 illustrates an experimental procedure for investigating the role of ADAMTS13 in hepatic ischemia/reperfusion injury.

As a result, it was found that both the marked increase of the vWF activity and the marked decrease of the ADAMTS13 activity occur at an early stage after liver transplantation (FIG. 7). Also, it was shown that vWF/ADAMTS13 imbalance occurred after liver transplantation in almost all cases (FIG. 8). From this, it was suggested that severe liver damage was potentially in the state of pre-TMA. Namely, it was suggested that organ dysfunction after organ transplantation (Delayed Graft Function; DGF) was induced by microcirculation disturbance together with the formation of platelet thrombi in the transplanted liver/platelet decrease in peripheral blood. This is considered to be a lethal condition for partial liver transplantation in which the hepatic spare ability is insufficient.

Example 8

<Role of ADAMTS13 in Hepatic Ischemia/Reperfusion Injury: Investigation Using Knockout Mice and Wild Type Mice and Protective Effect of Gene Recombinant ADAMTS13>

Male ADAMTS13KO mice 26 (129/+$^{Ter}$/SvJcl-TgH NCVC; 8-12 weeks old, 25-30 g) were purchased from National Cerebral and Cardiovascular Center Research Institute (Osaka) and corresponding wild type mice were obtained from Japan CLEA (Osaka). A mouse model of partial warm hepatic IRI was used. All mice were generally anesthetized with isoflurane and the artery/portal venous blood supply to the left/middle liver lobes was interrupted. After 90 min of ischemia, ischemic lobes were reperfused. To investigate the impact of ADAMTS13, mice were given an intravenous injection of recombinant ADAMTS13 (kindly provided from THE CHEMO-SERO-THERAPEUTIC RESEARCH INSTITUTE; ADAMTS13W688X) prior to ischemia insult and before reperfusion (20 U/body, respectively), and then sacrificed 2, 6 and 24 hr after reperfusion. Controls were treated with PBS. Sham-operated mice underwent the same procedure, but without vascular occlusion. Mice were assigned into the following three groups.
Group 1: wild type mice+PBS
Group 2: knockout mice+PBS
Group 3: knockout mice+recombinant ADAMTS13

No difference in peripheral blood and serum transaminase was observed other than the ADAMTS13 activity between knockout mice and wild type mice.

TABLE 1

|  | ADAMTS13+/+ | ADAMTS13−/− |  |
|---|---|---|---|
| AST (IU/L) | 60.0 ± 10.0 | 52.40 ± 2.20 | n.s. |
| ALT (IU/L) | 20.66 ± 5.66 | 27.60 ± 1.32 | n.s. |
| Hb (g/dl) | 16.05 ± 0.15 | 15.98 ± 0.47 | n.s. |
| Hct (%) | 54.10 ± 1.30 | 58.44 ± 2.2 | n.s. |
| Plt (×10$^4$/ul) | 67.90 ± 4.0 | 69.94 ± 6.86 | n.s. |
| ADAMTS13 (%) | 92.50 ± 2.5 | 3.46 ± 0.91 | p < 0.0001 |
| PT (sec) | 0.766 ± 0.004 | 0.786 ± 0.007 | n.s. |
| APTT (sec) | 23.80 ± 0.764 | 22.86 ± 0.898 | n.s. |
| PT (INR) | 0.766 ± 0.004 | 0.786 ± 0.007 | n.s. |

Liver Enzymes and Platelet Count:
Serum aspartate aminotransferase (sAST), alanine aminotransferase (sALT) and lactate hydrogenase (LDH) levels were measured by a standard spectrophotometric method with an automated clinical analyzer (JCA-BM9030, JEOL Ltd., Tokyo, Japan). Platelet count was quantified by Becton Dickinson QBC II Plus 4452 Automatic Blood Cell Counter.

Histology:
Liver paraffin embedded sections (4-μm thick) were stained with hematoxylin and eosin. The severity of liver IRI (necrosis, sinusoidal congestion, and vacuolization) was blindly graded with Suzuki's criteria on a scale from 0-429.
Quantitative Analysis of Microcirculation of the Liver:
The microcirculation of the liver after reperfusion was assessed by laser Doppler flowmetry (O2C: oxygen to see; LEA Medizintechnik GmbH, Giessen, Germany). Relative change of the blood flow against pre-ischemic value was calculated.
Measurement of Plasma ADAMTS13 Activity:
FRETS VWF73 method was used. Briefly, plasma samples were diluted in the reaction buffer (5 mM bis-Tris, 25 mM $CaCl_2$, and 0.05% Tween-20 at pH 6.0), then 4 μM FRETS-VWF73 (PEPTIDE INSTITUTE, INC., Osaka, Japan) substrate solution and 10 μl protease inhibitor cocktail (P8340, Sigma-Aldrich Inc., St Louis, USA) were added. After incubation, the emitted fluorescence intensity was measured using naïve wild type mice plasma as the standard by a fluorescence spectrophotometer (Fluoroskan Ascent F L, Thermo Labsystems, Helsinki, Finland) with excitation at 355 nm and emission at 460 nm.
Immunofluorescence for CD42b:
After deparaffinization of the liver sections, antigen was retrieved by citrate buffer (10 mM, pH 6.0). After blocking with Protein Block Serum-Free (X0909, DAKO, Tokyo, Japan) for 30 minutes, the sections were incubated with primary rabbit anti-mouse CD42b (bs-2347R, Boston, Mass.) at 1:200 dilution overnight at 4° C. Subsequently, the sections were reacted with Alexa Fluor@ 594 conjugated goat anti-rabbit IgG (H+L) secondary antibody. CD42b positive area was quantified by analysis software (Image J, NIH, USA). Negative control slides were prepared by the incubation with normal rabbit IgG (sc-2027, Santa Cruz, Calif.) instead of the first antibody.
SYBR Green Real-Time Reverse-Transcription Polymerase Chain Reaction:
Total RNA was extracted from the liver tissue using the RNeasy Kit (Qiagen, Venlo, Netherlands) and complementary DNA was prepared by Omniscript RT kit (Qiagen). Quantitative PCR was performed using the StepOnePlus™ Real-Time PCR System (Applied Biosystems®, Tokyo, Japan) with Fast SYBRR Green Master Mix. Amplification conditions were: 95° C. (20 sec), 95° C. (3 sec), followed by 45 cycles of 95° C. (15 sec), 60° C. (30 sec). Target gene expressions were calculated by their ratios to the housekeeping gene GAPDH.
Statistical Analysis:
All data are expressed as means±SEM. Differences between experimental groups were analyzed using two-way analysis of variance followed by Bonferroni's post-test or Student t test for unpaired data. All calculations were performed using GraphPad Prism 5 (GraphPad Software Inc., La Jolla, Calif., USA). All differences were considered statistically significant at the P value of <0.05.
Results:
(1) ADAMTS13 Expression is Down-Regulated in the Liver Upon IRI:
The plasma ADAMTS13 activity and quantification of mRNA of ADAMTS13 in the liver of wild type mice exposed to 90 minutes warm ischemia were examined. The concentration of ADAMTS13 in plasma fell down to about 36% at an early stage of reperfusion as compared in physiological condition, then such a low level was sustained with the duration up to 24 hours after reperfusion (FIG. 11). The gene expression of ADAMTS13 quantified RT-PCR decreased from the time point of ischemia, then being suppressed during IRI (FIG. 11). These results indicated that production of ADAMTS13 from HSCs was susceptible to ischemia and HSCs were vulnerable to liver IRI.

(2) ADAMTS13 Deficiency Exacerbates Liver Damage and Thrombocytopenia:

The liver function was analyzed in the model of 90 min partial liver warm ischemia followed by reperfusion. The damage due to IR was profoundly exacerbated in ADAMTS13−/− mice, compared with wild type. As shown in FIG. 11, the sAST at 24 hours, sALT at 6 hours and LDH levels both at 6 and 24 hours after reperfusion significantly increased. Consistent with liver damage, platelet count of peripheral blood decreased after reperfusion in ADAMTS13−/− mice (FIG. 11).

(3) Supplementation of ADAMTS13 Ameliorates IR-Induced Tissue Damage and Platelet Count:

To elucidate the function of ADAMTS13 during liver IR, the recombinant ADAMTS13 was administered intravenously into knockout mice before ischemia insult and just before reperfusion. As shown in FIG. 14, the sAST, sALT and LDH levels both 6 and 24 hours in knockout mice treated with the recombinant ADAMTS13 remarkably decreased after reperfusion as compared to knockout mice without recombinant ADAMTS13 treatment. Thus, the treatment with ADAMTS13 ameliorated fulminant hepatocellular damage in knockout mice. In histological findings shown in FIG. 15, the livers in PBS-treated knockout mice showed severe lobular edema, congestion, ballooning and necrosis. In contrast, the deteriorated liver damages in knockout mice were significantly improved both at 6 and 24 hours after reperfusion by the supplementation of the recombinant ADAMTS13. As consistent with liver enzymes, platelet count of peripheral blood was also profoundly ameliorated by recombinant ADAMTS13 administration both 6 and 24 hours in mice compared with mice without recombinant ADAMTS13 treatment.

(4) Platelet Aggregation within the Sinusoidal Space:

CD42b staining of the liver revealed that knockout mice treated with vehicle showed massive aggregation of platelet in sinusoidal space as compared to wild type mice. As shown in FIGS. 12 and 13, CD42b positive area was significantly reduced by recombinant ADAMTS13 administration in knockout mice. CD42b positive area was up-regulated along with the decrease of platelet count of peripheral blood, indicating that platelet aggregation occurred in the liver during IRI.

(5) ADAMTS13 Determines the Regulation of Hepatic Microcirculation in the Liver Dose Dependent Manner:

At 24 hour after reperfusion, hepatic blood flow of the liver in knockout mice without recombinant ADAMTS13 treatment significantly fell down to about 38% as compared to wild type mice. On the contrary, administration of the recombinant ADAMTS13 significantly ameliorated the intrahepatic microcirculation in knockout mice at 2 h. This data was correlated with the plasma activity of ADAMTS13 implying that ADAMTS13 determines the severity of IRI induced by the disturbance of microcirculation.

(6) ADAMTS13 Engagement Suppresses Inflammatory Cytokines and Chemokine Program:

The effects of ADAMTS13 deficiency and recombinant ADANTS13 treatment on the expression of cytokines and chemokine in liver tissues at 6 and 24 hours after reperfusion were investigated. Cytokines (TNF-α, IL-1β and IL-6) and chemokine ligand (CXCL-2) were measured by quantitative RT-PCR (FIG. 17). Six hours after reperfusion, ADAMTS13 deficiency profoundly increased the expression of IL-1β and IL-6 as compared with wild type mice. On the contrary, ADAMTS13 treatment significantly reduced TNF-α, IL-1β, IL-6 and CXCL-2 release at 6 h in knockout mice. These results indicated that ADAMTS13 possessed powerful anti-inflammatory effect on liver IRI.

Example 9

<Role of ADAMTS13 in hepatic ischemia/reperfusion injury: Investigation whether gene recombinant ADAMTS13 can exert protective effect on wild type mice in place of ADAMTS13 deficient mice>

Using the same procedures as in Example 8, whether protective effect to hepatic ischemia/reperfusion injury can be seen by administration of the recombinant ADAMTS13 to wild type mice was investigated. The mice were divided into the following two groups.

Group 1: wild type mice+PBS
Group 2: wild type mice+recombinant ADAMTS13

<Both Marked Increase of vWF Activity and Marked Decrease of ADAMTS13 Activity Occur by Hepatic Ischemia/Reperfusion>

In the above-described two groups, the liver tissue was collected before hepatic ischemia and reperfusion (pre), at the end of ischemia (immediately before reperfusion: 0 h), 2 hours after reperfusion (2 h), 6 hours after reperfusion (6 h), and 24 hours after reperfusion (24 h), and the gene expression of vWF and ADAMTS13 was quantified by quantitative RT-PCR. The results are shown as a relative ratio to GAPDH, house-keeping gene.

As a result, it was found that both marked increase of the vWF activity and marked decrease of the ADAMTS13 activity occurred in hepatic ischemia/reperfusion injury (FIG. 10). Thus, also in wild type mice (=normal adult), vWF/ADAMTS13 imbalance was significant and thus therapeutic significance of ADAMTS13 supplementation is greatly expected.

(1) ADAMTS13 Expression was Down-Regulated in the Liver Upon IRI:

Quantification of mRNA of ADAMTS13 in the liver of wild type mice exposed to 90 minutes warm ischemia was performed. As a result, the ADAMTS13 expression at the end of ischemia fell down to ¼ to ⅕ as compared to before ischemia and such a low level was sustained with the duration up to 24 hours after reperfusion (FIG. 10). Thus, it was shown that the hepatic stellate cells, which are ADAMTS13-producing cells, were damaged by hepatic ischemia/reperfusion and the systemic ADAMTS13 activity value markedly decreased.

(2) ADAMTS13 Deficiency Exacerbated Liver Damage and Thrombocytopenia:

Excess expression of vWF, which becomes a nucleus of platelet thrombus, and marked decrease in ADAMTS13, which is an enzyme cleaving platelet thrombus, significantly decreased the platelet count after IR. This platelet decrease was significantly ameliorated by administration of rADAMTS13. This significantly decreased the LDH elevation by hepatic microangiopathy (FIG. 23). As it turned out, due to amelioration of microangiopathy, hepatic deviation enzymes such as AST and ALT were significantly low in the rADAMTS13 administration group (FIG. 25).

(3) In histological findings, the livers in PBS-treated wild type mice showed severe lobular edema, congestion, ballooning and necrosis. In contrast, the deteriorated liver damages in wild mice were significantly improved both at 6 and 24 hours after reperfusion by the supplementation of the recombinant ADAMTS13. As consistent with the liver enzymes, platelet count of peripheral blood was also profoundly ameliorated by rADAMTS13 administration both 6 and 24 hours in wild type mice as compared to mice without the recombinant ADAMTS13.

(4) Platelet Aggregation within the Sinusoidal Space:

CD42b positive area was significantly reduced by recombinant ADAMTS13 administration in wild type mice. CD42b positive area indicated that platelet aggregation occurred in the liver during IRI.

(5) ADAMTS13 Determined the Regulation of Hepatic Microcirculation in the Liver Dose Dependent Manner:

Administration of the recombinant ADAMTS13 significantly ameliorated the intrahepatic microcirculation in wild type mice at 2 h. This data was correlated with the plasma activity of ADAMTS13 implying that ADAMTS13 determines the severity of IRI induced by the disturbance of microcirculation.

(6) ADAMTS13 Engagement Suppressed Inflammatory Cytokines and Chemokine Program:

The effects of ADAMTS13 deficiency and recombinant ADANTS13 treatment on the expression of cytokines and chemokine in liver tissues at 6 and 24 hours after reperfusion were investigated. Cytokines (TNF-α, IL-1β and IL-6) and chemokine ligand (CXCL-2) were measured by quantitative RT-PCR. ADAMTS13 treatment significantly reduced TNF-α, IL-1β, IL-6 and CXCL-2 release at 6 h in wild type mice. These results indicated that ADAMTS13 possessed powerful anti-inflammatory effect on liver IRI.

Example 10

<Role of ADAMTS13 in Liver Transplantation: Investigation Using 20% Partial Liver Transplantation Model and Protective Effect of Gene Recombinant ADAMTS13>

Since the ADAMTS13 activity produced by the stellate cells markedly decreases by cold storage inevitable for liver transplantation (FIG. 1) and, the smaller a size of transplanted liver is, the lower the ADAMTS13 activity becomes at an early stage after surgery (FIGS. 5 and 6), vWF/ADAMTS13 imbalance is observed in all the case after liver transplantation to a greater or lesser extent (FIG. 7) and is extreme in the case of early death (FIG. 8). Viewing this, using rat partial liver transplantation model, the present inventors investigated protective effect when the recombinant ADAMTS13 is administered after adult living donor liver transplantation. As an animal model mimicking adult living donor liver transplantation, a rat allograft 20% partial liver graft model was prepared using Lewis rat (male, 250 to 300 g) and using right lobe plus caudate lobe alone as liver graft.

The survival rate on the fourth day after liver transplantation was 100% and excellent in specimen sampling, at the same time the seven-day survival was 60%, and the effect of the therapeutic effect on survival could be evaluated as a main end point. Administration of the recombinant ADAMTS13 significantly ameliorated the hepatocyte damage after 20% partial liver transplantation (FIG. 25). Also, administration of the recombinant ADAMTS13 significantly ameliorated the thrombotic microangiopathy (TMA conditions) (FIG. 23). From the pathological point of view, the normality of the transplanted liver was maintained by administration of the recombinant ADAMTS13 to a model of 20% partial liver transplantation (FIG. 26).

INDUSTRIAL APPLICABILITY

The present invention relates to new use of a whole length or its partial fragment of ADAMTS13. By using ADAMTS13 in accordance with the present invention, it becomes possible to diagnose quickly and accurately acute and chronic liver damage and to provide an agent for effectively treating liver damage, hepatic ischemia/reperfusion injury, hepatic dysfunction after liver transplantation and acute liver failure/fulminant hepatitis.

The invention claimed is:

1. A method of testing and treating a disorder of hepatic non-parenchymal cells, comprising:

measuring or monitoring the ADAMTS13 activity in a sample from a mammal, wherein the disorder of hepatic non-parenchymal cells is a disorder after chemotherapy of colorectal cancer, and wherein the mammal is diagnosed with the disorder of hepatic non-parenchymal cells when a decrease in the ADAMTS13 activity in the sample is observed as compared to the ADAMTS13 activity in a sample from a healthy subject, and treating the mammal diagnosed with the disorder of hepatic non-parenchymal cells by administering ADAMTS13 or a mutant of ADAMTS13 having ADAMTS13 activity as an effective ingredient, or a pharmaceutical composition comprising ADAMTS13 or a mutant of ADAMTS13 having ADAMTS13 activity as an effective ingredient.

2. The method of claim 1, wherein the mammal is human.

3. The method of claim 1, wherein the sample from a mammal is blood from a mammal.

4. The method of claim 1, wherein the mutant of ADAMTS13 is a molecule comprising a minimum unit necessary for exerting ADAMTS13 activity, wherein the minimum unit consists of a portion of ADAMTS13 from the metalloprotease domain to a spacer domain.

5. The method of claim 4, wherein the mutant of ADAMTS13 is a C-terminus deficient mutant W688X (ADAMTS13W688X protein) which is a resultant of deletion of the C-terminal portion from the amino acid at position 689 from ADAMTS13 consisting of 1427 amino acid residues.

6. The method of claim 1, wherein the administration of ADAMTS13 or the mutant of ADAMTS13 is systemic administration or topical administration.

7. The method of claim 6, wherein systemic administration is selected from the group consisting of oral, subdermal, intramuscular, intraperitoneal, subcutaneous, nasal, sublingual and rectal administration.

8. The method of claim 1, wherein the pharmaceutical composition is administered orally and is selected from the group consisting of tablets, capsules, powders, and liquids.

9. The method of claim 8, wherein the tablets comprise ADAMTS13 or a mutant of ADAMTS13 having ADAMTS13 activity, and gelatin or adjuvants.

10. The method of claim 8, wherein the liquids comprise ADAMTS13 or a mutant of ADAMTS13 having ADAMTS13 activity, and a liquid carrier selected from the group consisting of water, petroleum, animal oils, vegetable oils, mineral oils, synthetic oils, saline, a solution of glucose, a solution of ethylene glycol, a solution of propylene glycol, and a solution of polyethylene glycol.

11. The method of claim 1, wherein the pharmaceutical composition is administered by intravenous, cutaneous, or subcutaneous injection, and the pharmaceutical composition comprises ADAMTS13 or a mutant of ADAMTS13 having ADAMTS13 activity, and a solution comprising at least one additional component selected from the group consisting of isotonic media, a preservative, a stabilizing agent, a buffer, an antioxidant and other pharmaceutically acceptable additives.

12. The method of claim 1, wherein the pharmaceutical composition is administered in an amount of 100 to 700 units/kg body weight by intravenous injection, intramuscular injection, or subcutaneous injection, and is administered one or more times.

* * * * *